United States Patent
Kondo et al.

(10) Patent No.: US 9,297,020 B2
(45) Date of Patent: Mar. 29, 2016

(54) GENE FOR INCREASING THE PRODUCTION OF PLANT BIOMASS AND METHOD OF USE THEREOF

(75) Inventors: Satoshi Kondo, Miyoshi (JP); Etsuko Hattori, Toyota (JP); Chikara Ohto, Toyota (JP); Norihiro Mitsukawa, Miyoshi (JP); Kenichi Ogawa, Kyoto (JP)

(73) Assignees: TOYOTA JIDOSHA KABUSHIKI KAISHA, Aichi (JP); OKAYAMA PREFECTURE, Okayama (JP)

( * ) Notice: Subject to any disclaimer, the term of this patent is extended or adjusted under 35 U.S.C. 154(b) by 187 days.

(21) Appl. No.: 13/128,373

(22) PCT Filed: Nov. 11, 2009

(86) PCT No.: PCT/JP2009/069155
§ 371 (c)(1),
(2), (4) Date: May 9, 2011

(87) PCT Pub. No.: WO2010/055837
PCT Pub. Date: May 20, 2010

(65) Prior Publication Data
US 2011/0225677 A1 Sep. 15, 2011

(30) Foreign Application Priority Data

Nov. 11, 2008 (JP) ................................. 2008-288869

(51) Int. Cl.
*C12N 15/82* (2006.01)
*C07K 14/415* (2006.01)

(52) U.S. Cl.
CPC .......... *C12N 15/8261* (2013.01); *C07K 14/415* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 7,176,351 B2 | 2/2007 | Kisaka et al. | |
| 2006/0183137 A1* | 8/2006 | Harper et al. | 435/6 |
| 2006/0225154 A1* | 10/2006 | Kasukabe et al. | 800/289 |
| 2007/0256194 A1 | 11/2007 | Allefs et al. | |
| 2008/0040972 A1 | 2/2008 | Chalivendra et al. | |
| 2008/0057093 A1 | 3/2008 | Wan et al. | |
| 2008/0113342 A1* | 5/2008 | Cao et al. | 435/6 |
| 2008/0227639 A1 | 9/2008 | Wu et al. | |
| 2008/0254989 A1 | 10/2008 | Cherian | |
| 2009/0019602 A1 | 1/2009 | Sheen et al. | |
| 2009/0126046 A1 | 5/2009 | Valerie | |
| 2009/0138991 A1 | 5/2009 | Reuzeau | |
| 2012/0159666 A1 | 6/2012 | Yonekura et al. | |

FOREIGN PATENT DOCUMENTS

| | | |
|---|---|---|
| CN | 101182353 A | 5/2008 |
| JP | 8266179 | 10/1996 |
| JP | 9-503389 A | 4/1997 |
| JP | 2000-515020 A | 11/2000 |
| JP | 2001-50541 A | 4/2001 |
| JP | 2001252084 | 9/2001 |
| JP | 2001-519659 A | 10/2001 |
| JP | 2005-52114 A | 3/2005 |
| JP | 2005-130770 A | 5/2005 |
| JP | 2007-530063 A | 11/2007 |
| JP | 2001-505410 A | 6/2011 |
| WO | 95/09911 A1 | 4/1995 |
| WO | 98/03631 A1 | 1/1998 |
| WO | 98/10082 A1 | 3/1998 |
| WO | 98/42851 A1 | 10/1998 |
| WO | 98/59039 A1 | 12/1998 |
| WO | 2004/104162 A2 | 12/2004 |
| WO | 2005/094562 A1 | 10/2005 |
| WO | 2006/005771 A1 | 1/2006 |
| WO | 2006/069017 A2 | 6/2006 |
| WO | WO 2006/131547 * | 12/2006 |
| WO | 2007/020638 A2 | 2/2007 |
| WO | 2008/061153 A1 | 5/2008 |
| WO | 2008/062049 A1 | 5/2008 |
| WO | 2008/116829 | 10/2008 |
| WO | 2009/060418 | 5/2009 |

OTHER PUBLICATIONS

Rizhsky et al., Plant Phys 134:1683-96 (2004).*
Swarbreck et al., AEE74273, 2000.*
Magome et al., Plant J 56:613-26 (2008).*
Wahl et al. (Meth Enzymol 152:399-407 (1987).*
Shiu & Bleecker, Plant Phys 132:530 (2003).*
Kasuga_Plant Cell Physiol_45_346_(2004).*
Salanoubat et al_AEE74273_2000.*
Rizhsky et al. (Plant Phys 134:1683-96 (2004).*
Magome et al. (Plant J 56:613-26 (2008).*
Tuteja (Meth Enzymol 428:419-38 (2007).*
Guodong Wang, et al., "A Genome-Wide Functional Investigation into the Roles of Receptor-Like Proteins in Arabidopsis", Plant Physiology, Jun. 2008, pp. 503-517, vol. 147.
Jas Singh, et al., "The GLK1 'Regulon' Encodes Disease Defense Related Proteins and Confers Resistance to Fusarium Graminearum in Arabidopsis", Cereal Res. Commun., 2008, pp. 261-265, vol. 36, Suppl. B.
Ludmila Rizhsky, et al., "When Defense Pathways Collide: The Response of Arabidopsis to a Combination of Drought and Heat Stress", Plant Physiology, 2004, pp. 1-14, vol. 134.
Shin-Han Shiu, et al., "Expansion of the Receptor-Like Kinase/Pelle Gene Family and Receptor-Like Proteins in Arabidopsis", Plant Physiology, Jun. 2003, pp. 530-543, vol. 132.

(Continued)

*Primary Examiner* — Medina A Ibrahim
*Assistant Examiner* — Russell Boggs
(74) *Attorney, Agent, or Firm* — Sughrue Mion, PLLC

(57) ABSTRACT

A technique by which the production of plant biomass can be significantly increased is provided. The AT3G05660 gene encoding a receptor-like protein having a leucine-rich repeat structure or a gene functionally equivalent to such a gene is introduced, or an expression control region of an endogenous gene corresponding to the gene is modified.

8 Claims, 5 Drawing Sheets

(56) References Cited

OTHER PUBLICATIONS

Hiroshi Magome, et al., "The DDF1 Transcriptional Activator Upregulates Expression of a Gibberellin-Deactivating Gene, GA2ox7, Under High-Salinity Stress in Arabidopsis", The Plant Journal, 2008, pp. 613-626, vol. 56.

Bostjan Kobe, et al., "The Leucine-Rich Repeat as a Protein Recognition Motif", National Diet Library, Apr. 3, 2011.

Meyer et al., "A leucine-rich repeat protein of carrot that exhibits antifreeze activity", FEBS Letters, 447:171-178 (1999).

Osakabe et al., "Functional analysis of a leucine-rich repeat receptor like kinase, RPK1, involved in ABA signal transduction of Arabidopsis", CD p. 4T17-10(4P-1263), 2008.

Arabidopsis thaliana AtRLP28 (Receptor Like Protein 28); protein binding (AtRLP28) mRNA, complete CDS, NCBI Reference Sequence: NM_128868.1, http://www.ncbi.nlm.nih.gov/nuccore/18403183?sat=14&satkey=6644359, online Aug. 21, 2009, retrieved Apr. 26, 2013.

Tuteja, "Mechanisms of High Salinity Tolerance in Plants", Meth. Enzymol., 428:419-38 (2007) [Abstract, Figures and Legends only].

Notice of Allowance issued on Jan. 13, 2014 for U.S. Appl. No. 13/120,901.

GenBank Accession No. Q8W3K0. Probable disease resistance protein At1g58602. Published Apr. 29, 2008, pp. 1-4.

Notice of Allowance, dated Apr. 21, 2014, issued by the United States Patent and Trademark Office, in counterpart U.S. Appl. No. 13/120,901.

Michael B. Cooley, et al., "Members of the Arabidopsis HRT/RPP8 Family of Resistance Genes Confer Resistance to Both Viral and Oomycete Pathogens", The Plant Cell, 2000, pp. 663-676, vol. 12.

Jennifer M. Lorang, et al., "Plant disease Susceptibility Conferred by a "Resistance" Gene", Proc. Natl. Acad. Sci. USA, 2007, pp. 14861-14866, vol. 104 No. 37.

Blake C. Meyers, et al., "Genome-Wide Analysis of NBS-LRR-Encoding Genes in Arabidopsis", The Plant Cell, Apr. 2003, pp. 809-834, vol. 15.

Kristen R. Jaglo-Ottosen, et al., "Arabidopsis CBF1 Overexpression Induces COR Genes and Enhances Freezing Tolerance", Science, Apr. 3, 1998, pp. 104-106, vol. 280.

Andrea Chini, et al., "Drought Tolerance Established by Enhanced Expression of the CC-NBS-LRR Gene, ADR1, Requires Salicylic Acid, EDS1 and ABI1", The Plant Journal, 2004, pp. 810-822, vol. 38.

Youssef Belkhadir, et al., "Plant Disease Resistance Protein Signaling: NBS-LRR Proteins and Their Partners", Current Opinion in Plant Biology, 2004, pp. 391-399.

Yasuhiro Kadota, et al., "Protein, Nucleic Acid and Enzyme (PNE)", 2007, pp. 718-723, vol. 52, No. 6.

Mie Kasuga, et al., "Improving Plant Drought, Salt, and Freezing Tolerance by Gene Transfer of a Single Stress-Inducible Transcription Factor", Nature Biotechnology, Mar. 1999, pp. 287-291, vol. 17.

Qiang Liu, et al., "Two Transcription Factors, DREB1 and DREB2, with an EREBP/AP2 DNA Binding Domain Separate Two Cellular Signal Transduction Pathways in Drought-and Low-Temperature-Responsive Gene Expression, Respectively, in Arabidopsis", The Planet Cell, Aug. 1998, pp. 1391-1406, vol. 10.

Stephen T. Chisholm, et al, "Host-Microbe Interactions: Shaping the Evolution of the Plant Immune Response", Cell, Feb. 24, 2006, pp. 803-814.

Lin et al., "Putative Leucine-Rich Repeat Disease Resistance Protein", Database Accession No. 049327, XP002615233 (Jun. 1, 1998).

Lin et al., "Putative Leucine-Rich Repeat Disease Resistance Protein", Database Accession No. 049325, XP002615234 (Jun. 1, 1998).

Lin et al., "Putatie Leucine-Rich Repeat Disease Resistance Protein", Database Accession No. 049328, XP002615235 (Jun. 1, 1998).

Cheng et al., "New Changes in the Plasma-Membrane-Associated Proteome of Rice Roots Under Salt Stress", Proteomics, 9(11):3100-3114 (2009).

Hong et al., "Identification of a Receptor-Like Protein Kinase Gene Rapidly Induced by Abscisic Acid, Dehydration, High Salt, and Cold Treatments in Arabidopsis Thaliana", Plant Physiology, 113(4):1203 1212 (1997).

De Lorenzo et al., "A Novel Leucine-Rich Repeat Receptor Kinase Regulates the Response of Medicago Truncatula Roots to Salt Stress", Plant Cell, 21(2):668-680 (2009).

Osakabe et al., "Leucine-Rich Repeat Receptor-Like Kinase1 Is a Key Membrane-Bound Regulator of Abscisic Acid Early Signaling in Arabidopsis", Plant Cell, 17:1105-1119 (2005).

Tamura et al., "Osmotic Stress Tolerance of Transgenic Tobacco Expressing a Gene Encoding a Membrane-Located Receptor-Like Protein from Tobacco Plants", Plant Physiology, 131:454-462 (2003).

Rounsley et al., Arabidopis thaliana—putative leucine-rich repeat disease resistance protein, GenBank Accession No. AAC04912.1, PLN Mar. 11, 2002.

Peart et al. Ubiquitin ligase-associated protein SGT1 is required for host and nonhost disease resistance in plants. PNAS. 2002. 99(16): 10865-10869.

Kennel. Principles and practices of nucleic acid hybridization. Progress in Nucleic Acid Research and Molecular Biology. 1971. 11:259-301.

Maniatis et al. Molecular Cloning. Cold Spring Harbor Laboratory. 1982. pp. 324-389.

Weigel et al. Activation tagging in Arabidopsis. Plant Physiology. 2000. 122: 1003-1013.

Leister. Tandem and segmental gene duplication and recombination in the evolution of plant disease resistance genes. TRENDS in Genetics. 2004. 20(3): 116-122.

Sweat et al. Characterization of natural and induced variation in the LOV1 gene, a CC-NBS-LRR gene conferring victorin sensitivity and disease susceptibility in Arabidopsis. MPMI. 2008. 21(1): 7-19.

GenBank Acession No. NM-001084273.1. Published Apr. 20, 2007.

Theologis et al. GenBank Accession No. NM-001084273.2. Published May 28, 2011.

GenBank Accession No. AEM36350.At1g58602. Published Oct. 11, 2011. pp. 1-2.

Official Office Action for U.S. Appl. No. 13/120,901 issued on Sep. 26, 2012.

Official Office Action for U.S. Appl. No. 13/120,901 issued on Feb. 15, 2013.

Official Office Action for U.S. Appl. No. 13/120,901 issued on Jul. 30, 2013.

Lin et al., "Putative disease resistance protein [Arabidopsis thaliana]," GenBank AAF26131.1, Oct. 8, 1999.

Zhang, Hong-Xia, et al., "Engineering Salt-Tolerant *Brassica* Plants: Characterization of Yield and Seed Oil Quality in Transgenic Plants with Increased Vacuolar Sodium Accumulation," PNAS, vol. 98, No. 22, Oct. 23, 2001, pp. 12832-12836.

Sahi, Chandan, et al., "Salt Stress Response in Rice: Genetics, Molecular Biology, and Comparative Genomics," Funct. Integr. Genomics, vol. 6, 2006, pp. 263-284.

Abdin, MZ, et al., "Abiotic Stress Related Genes and their Role in Conferring Resistance in Plants," Indian Journal of Biotechnology, col. 1, Jul. 2002, pp. 225-244.

UniPro Database, Direct submission, Accession No. 049325, Jun. 1, 1998.

Communication, dated Oct. 1, 2015, issued by the United States Patent and Trademark Office in U.S. Appl. No. 13/504,834.

\* cited by examiner

Fig. 1

```
AT3G05660    --------MSLIPITFY--FLFLFFSNFRGVFAVPNIHLCHFEQRDALLEFKNEFKIKKPC
AT3G05650    MKDSWNSTSIIPFTFSSLIFFLFTFDFQDVFGVPTKHLCRLEQRDALLELKKEFKIKKPC
              *:**:**   ::***  :*:.**.**. ***::*******:*:********

AT3G05660    FGCPSPLKTKSWENGSDCCHWDGITCDAKTGEVIEIDLMCSCLHGWFHSNSNLSMLQNFH
AT3G05650    FDGLHP-TTESWANNSDCCYWDGITCNDKSGEVLELDLSRSCLQSRFHSNSSLFTVLNLR
              *.   *  *:*** *.*****:******: *:***:*:** ***:. *****.*  : *::

AT3G05660    FLTTLDLSYNHLSGQISSSIGNLSHLTTLDLSGNNFSGWIPSSLGNLFHLTSLHLYDNNF
AT3G05650    FLTTLDLSYNYFSGQIPSCIENFSHLTTLDLSKNYFS-----------------------
             **********::****.*.* *:*********.* **
                    ┌ Region A
AT3G05660    GGEIPSSLGNLSYLTFLDLSTNNFVGEIPSSFGSLNQLSILRLDNNKLSGNLPLEVINLT
AT3G05650    -GGIPSSIGNLSQLTFLDLSGNEFVGEMP-FFGNMNQLTNLYVDSNDLTGIFPLSLLNLK
              * ****:**** *******: ****:*   **.:***:* :*.*.*:* :**..::**.

AT3G05660    KLSEISLSHNQFTGTLPPNITSLSILESFSASGNNFVGTIPSSLFTIPSITLIFLDNNQL
AT3G05650    HLSDLSLSRNQFTGTLPSNMSSLSNLEYFEAWGNAFTGTLPSSLFTIASLTSINLRNNQL
             :**::***:********.*:.***:**:** *.* ** *.**:*******.*:* * * ****

AT3G05660    SGTLEFGNISSPSNLLVLQLGGNNLRGPIPTSISRLVNLRTLDLSHFNIQGGVDFNIFSH
AT3G05650    NGTLEFGNISSPSTLTVLDISNNNFIGPIPKSISKFINLQDLDLSHLNTQGPVDFSIFTN
             .************.* * **::..**:  ****.***:::**:  *****:* ** ***.**::

AT3G05660    LKLLGNLYLSHSNTTTTIDLNAVLS-CFKMLISLDLSGNHVLVTNKSSVSDP-PLGLIGS
AT3G05650    LKSLQLLNLSHLNTTTTIDLNALFSSHLNSIYSMDLSGNHVSATTKISVADHHPTQLISQ
             ** *  * ***  ***********:*   ::  :  *:*******  .*.* **:*    **..

AT3G05660    LNLSGCGITEFPDILRTQRQMRTLDISNNKIKGQVP--SWLLLQLEYMHISNNNFIGFER
AT3G05650    LYLSGCGITEFPELLRSQHKMTNLDISNNKIKGQVPGWLWTLPKLIFVDLSNNIFTGFER
             * *************::**:*::* .*************   * *  :*  :: :*** * ****

AT3G05660    STKLEKTVVPKPSMKHFFGSNNNFSGKIPSFICSLRSLIILDLSNNNFSGAIPPCVGKFK
AT3G05650    STEHGLSLITKPSMQYLVGSNNNFTGKIPSFICALRSLITLDLSDNNLNGSIPPCMGNLK
             **:   :::.****::.*******.********:***** ****:**:.*:****:*:.*

AT3G05660    STLSDLNLRRNRLSGSLPKTIIKSLRSLDVSHNELEGKLPRSLIHFSTLEVLNVESNRIN
AT3G05650    STLSFLNLRQNRLGGGLPRSIFKSLRSLDVGHNQLVGKLPRSFIRLSALEVLNVENNRIN
             **** ****:***.*.**::*.:********.**:*.******.**:. :*:*******.****

AT3G05660    DTFPFWLSSLKKLQVLVLRSNAFHGRIHKTRFPKLRIIDISRNHFNGTLPSDCFVEWTGM
AT3G05650    DTFPFWLSSLKKLQVLVLRSNAFHGPIHHASFHTLRIINLSHNQFSGTLPANYFVNWNAM
             *************************.**::  *  . ****:*:*:*.****::  **:*. *

AT3G05660    HSLEKNEDRFNEKYMGS--GYYHDSMVLMNKGLEMELVRILKIYTALDFSGNKFEGEIPR
AT3G05650    SSLMATEDRSQEKYMGDSFRYYHDSVVLMNKGLEMELVRILKIYTALDFSENKLEGEIPR
              **  .*** :*****.    *****:******************** **::**.******

AT3G05660    SIGLLKELHILNLSSNGFTGHIPSSMGNLRELESLDVSRNKLSGEIPQELGNLSYLAYMN
AT3G05650    SIGLLKELHVLNLSSNAFTGHIPSSMGNLRELESLDVSQNKLSGEIPQELGNLSYLAYMN
             *********:******.********************:*********************

AT3G05660    FSHNQLVGQVPGGTQFRTQSASSFEENLGLCGRPLEE-CRVVHEPTPSG-ESETLESE--
AT3G05650    FSHNQLGGLVPGGTQFRRQNCSSFKDNPGLYGSSLEEVCLDIHAPAPQQHEPPELEEEDR
             ****** * ********* *..:***:.:**   *  .*** *  :* *:*. *. **.*

AT3G05660    QVLSWIAAAIGFTPGIVLGLTIGHIVLSSKPRWFFKVL-YINNSRRRRRTRSEKS
AT3G05650    EVFSWIAAAIGFGPGIAFGLTIRYILVFYKPDWFMHTFGHLQPSAHEKRLRRKQ-
             :*:********* ***.:**** : :* **:** :.    :   * **:*:*::
```

Fig. 2-1

```
AT3G05660    --------MSLIPITFY---FLFLFFSNFRGVFAVPNIHLCHFEQRDALLEFKNEFKIKKPC
AT3G05650    MKDSWNSTSIIPFTFSSLIFFLFTFDFQDVFGVPTKHLCRLEQRDALLELKKEFKIKKPC
AT2G33080    MSGSHLRLRFLSLLLLCCVSSSTSSLFTFSYPVLDLVACRSHQIQAFTQFKNEFDTHR--
                 ::,:        *  :*    *:,*,*:**.  ::

AT3G05660    FGCPSPLKTKSWENGSDCCHWDGITCDAKTGEVIEIDLMCSCLHGWFHSNSNLSMLQNFH
AT3G05650    FDGLHP-TTESWANNSDCCYWDGITCNDKSGEVLELDLSRSCLQSRFHSNSSLFTVLNLR
AT2G33080    ------------CNHSDHS--NGVWCDNSTGVVTKLQLN-ACLSGTLNPNSSLFWFHQLR
                     * **,  :*: *: ,:* *  ::* :**, ::,**,*  , :::

AT3G05660    FLTTLDLSYNHLSGQISSSIGNLSHLTTLDLSGNNFSGWIPSSLGNLFHLTSLHLYDNNF
AT3G05650    FLTTLDLSYNYFSGQIPSCIENFSHLTTLDLSKNYFS-----------------------
AT2G33080    FLN---LSHNNFTSTS--------------------------------------------
             **,   **:* ::.
            ┌ Region A
AT3G05660    GGEIPSSLGNLSYLTFLDLSTNNFVGEIPSSFGSLNQLSILRLDNNKLSGNLPLEVINLT
AT3G05650    -GGIPSSIGNLSQLTFLDLSGNEFVGEMP-FFGNMNQLTNLYVDSNDLTGIFPLSLLNLK
AT2G33080    ----FPSEFGNLNKVEVLDLSFNSFTGQVPSSFSNLSQLTELHLSNNQLTGGFP-QVQNLT
                 :,:*,  : ,**** *,*,*:*  *,.,**: * :.,*,*:*  :*  :   **, AT3G05660    KLSEISLSHNQFTGTLPPNITSLSILESFSASGNNFVGTIPSSLFTIPSITLIFLDNNQL
AT3G05650    HLSDLSLSRNQFTGTLPSNMSSLSNLEYFEAWGNAFTGLPSSLFTIASLTSINLRNNQL
AT2G33080    NLSHLDFENNKFSGTVPSSLLMMPFLSYLNLYGNHFTGSI---------------------
             :**,:,:,,*:*:**:*,,:  :, *, :,,  ** *,*::

AT3G05660    SGTLEFGNISSPSNLLVLQLGGNNLRGPIPTSISRLVNLRTLDLSHFNIQGQVDFNIFSH
AT3G05650    NGTLEFGNISSPSTLTVLDISNNNFIGPIPKSISKFINLQDLDLSHLNTQGPVDFSIFTN
AT2G33080    -------EVSTSSKLEILYLGLKPFEGQILEPISKLINLKRLELSFLNISYPLDLNLFSS
                    ::*:,*,* :* :,  ::  * **  ,**::**:  *:**,:*  ,  :*:,:*:

AT3G05660    LKLLGNLYLSHSNTTTTIDLNAVLS-CFKMLISLDLSGNHVLVTNKSSVSDP-PLGLIGS
AT3G05650    LKSLQLLNLSHLNTTTTIDLNALFSSHLNSIYSMDLSGNHVSATTKISVADHHPTQLISQ
AT2G33080    LKSLT---------------------YLDLSGNSISP--RSLRSDLYIPLTLEK
             ** *                       :*****  :     :*     :   :.

AT3G05660    LNLSGCGITEFPDILRTQRQMRTLDISNNKIKGQVP--SWLLLQLEYMHISNNNFIGFER
AT3G05650    LYLSGCGITEFPELLRSQHKMTNLDISNNKIKGQVPGWLWTLPKLIFVDLSNNIFTGFER
AT2G33080    LLLEQCGIIEFPNILKTLQKLEYIDMSNNRINGKIPEWLWRLPRLRSMSLANNSFNGFEG
             * *, *** ***::*:: :::  :*:***:*:** *  :*  :*  :  :,:** * ***

AT3G05660    STKLEKT---------------VVPKP--SMKHFFGSNNNFSGKIPSFICSLRSLIILDL
AT3G05650    STEHGLS---------------LITKP--SMQYLVGSNNNFTGKIPSFICALRSLITLDL
AT2G33080    STDVLVNSSMEILFMHSNNIQGALPNLPLSIKAFSAGYNNFSGEIPLSICNRSSLAALSL
             **,      ,           :,:  *:  :,, ***:*** ** ** *,*

AT3G05660    SNNNFSGAIPPCVGKFKSTLSDLNLRRNRLSGSLPKTIIK--SLRSLDVSHNELEGKLPR
AT3G05650    SDNNLNGSIPPCMGNLKSTLSFLNLRQNRLGGGLPRSIFK--SLRSLDVGHNQLVGKLPR
AT2G33080    PYNNFTGKIPQCL-----SNLTFVHLRKNNLEGSIPDTLCAGDSLQTLDIGFNLISGTLPR
             , **:,* ** *:     *,*: :,**:* :,*,:*:     :  **:,* : *,***

AT3G05660    SLIHFSTLEVLNVESNRINDTFPFWLSSLKKLQVLVLRSNAFHGRIHKTR-----FPKLR
AT3G05650    SFIRLSALEVLNVENNRINDTFPFWLSSLKKLQVLVLRSNAFHGPIHHAS-----FHTLR
AT2G33080    SLLNCSSLEFLSVDNNRIKDTFPFWLKALPNLQVLILSSNKLYGPIAPPHQSPLAFPELR
             *::, *:**, *,*:,*********, *  :*****:* ** ::* *     *  **
```

Fig. 2-2

```
AT3G05660    IIDISRNHFNGTLPSDCFVEWTGMHSLEKNEDR----FNEKYMGS--GYYHDSMVLMNK
AT3G05650    IINLSHNQFSGTLPANYFVNWNAMSSLMATEDR----SQEKYMGDSFRYYHDSVVLMNK
AT2G33080    IFEIADNMFTGTLSPRYFVNWK-TSSLTVNEDGDLYMVYKNNAFGIDSYVYRDTIDMKYK
             *:::: * *.***.. **:*. ** .**    ::: :*    *:*:: : *

AT3G05660    GLEMELVRILKIYTALDFSGNKFEGEIPRSIGLLKELHILNLSSNGFTGHIPSSMGNLRE
AT3G05650    GLEMELVRILKIYTALDFSENKLEGEIPRSIGLLKELHVLNLSSNAFTGHIPSSMGNLRE
AT2G33080    GLSMEQQMVLNSYSAIDFSGNRLEGQIPKSIGLLKELIALNLSNNAFTCHIPLSLANATE
             **.**   :*: *:*:*** *::**:**:******** ****.*.** *** *:.* *

AT3G05660    LESLDVSRNKLSGEIPQELGNLSYLAYMNFSHNQLVGQVPGGTQFRTQSASSFEENLGLC
AT3G05650    LESLDVSQNKLSGEIPQELGNLSYLAYMNFSHNQLGGLVPGGTQFRRQNCSSFKDNPGLY
AT2G33080    LESLDLSRNQLSGTIPNGLKTLSFLAYINVSHNKLKGENHKEHRLLGNINPPLKG-----
             *****:*:*:*** **: * .**:***:*.***:* *    ::  :  ..::

AT3G05660    GRPLEE-CRVVHEPTPSG-ESETLESE--QVLSWIAAAIGFTPGIVLGLTIGHIVLSSKP
AT3G05650    GSSLEEVCLDIHAPAPQQHEPPELEEEDREVFSWIAAAIGFGPGIAFGLTIRYILVFYKP
AT2G33080    ------------------------------------------------MQGFVVFLWRK
                                                             .::.  :

AT3G05660    RWFFKVL-YINNSRRRRRTRSEKS
AT3G05650    DWFMHTFGHLQPSAHEKRLRRKQ-
AT2G33080    LALERMRRQHNNLRKKTKNRSKC-
             : :     :  :. : * :
```

Wild-type plants    Transformed plants

GENE FOR INCREASING THE PRODUCTION OF PLANT BIOMASS AND METHOD OF USE THEREOF

CROSS REFERENCE TO RELATED APPLICATIONS

This application is a National Stage of International Application No. PCT/JP2009/069155 filed Nov. 11, 2009, claiming priority based on Japanese Patent Application No. 2008-288869, filed Nov. 11, 2008, the contents of all of which are incorporated herein by reference in their entirety.

TECHNICAL FIELD

The present invention relates to: a plant into which a given gene is introduced or the expression control region of the given endogenous gene corresponding to the gene is modified; a method for increasing the production of biomass through introduction of a given gene or modification of an expression control region of the given endogenous gene; and a method for producing a plant capable of producing an increased amount of biomass.

BACKGROUND ART

The term "biomass" generally refers to the total amount of organisms that inhabit or exist in a given area. When such term is used with regard to plants, in particular, it refers to dry weight per unit area. Biomass units are quantified in terms of mass or energy. The expression "biomass" is synonymous with "Seibutsutairyo" or "Seibutsuryo." In the case of plant biomass, the term "standing crop" is occasionally used for "biomass." Since plant biomass is generated by fixing atmospheric carbon dioxide with the use of solar energy, it can be regarded as so-called "carbon-neutral energy." Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

In particular, an energy crop such as sugar cane can be used as a raw material for biofuel. Hence, the increased production of the total mass of a plant itself (the amount of plant biomass) is expected. Under such circumstances, improvement in productivity per unit of cultivation area is required in order to increase the production of the amount of plant biomass. It has been found that if the number of cultivated plants is assumed to be constant per unit of cultivation area, improvement in the amount of biomass per plant would be necessary.

However, it is thought that since many genes are involved in the amount of plant biomass (a so-called "kind of quantitative trait"), individual gene introduction or individual genetic modification cannot lead to an effective increase in the production of plant biomass. Meanwhile, a great deal of difficulties are associated with introduction of many genes in a desired state into a plant. Such gene introduction is also problematic in that if successful gene introduction takes place, desirable traits cannot always be acquired.

Various gene transfer techniques are known as techniques for increasing the production of plant biomass, as disclosed in JP Patent Publication (Kohyo) No. 2001-505410 A; JP Patent Publication (Kohyo) No. 2001-519659 A; JP Patent Publication (Kohyo) No. 2007-530063 A; JP Patent Publication (Kokai) No. 2005-130770 A; JP Patent Publication (Kohyo) No. 2000-515020 A; JP Patent Publication (Kohyo) No. 9-503389 A (1997); and JP Patent Publication (Kokai) No. 2005-52114 A, for example. However, according to techniques disclosed in Patent Documents (JP Patent Publication (Kohyo) No. 2001-505410 A; JP Patent Publication (Kohyo) No. 2001-519659 A; JP Patent Publication (Kohyo) No. 2007-530063 A; JP Patent Publication (Kokai) No. 2005-130770 A; and JP Patent Publication (Kohyo) No. 2000-515020 A), only the effects of increasing the production of partial plant biomass, such as plant seeds, tubers, roots, and leaves, can be obtained. Also, techniques disclosed in JP Patent Publication (Kohyo) No. 9-503389 A (1997) and JP Patent Publication (Kokai) No. 2005-52114 A disclose only the effects of increasing the production of biomass under nitrate-unlimited growth conditions or by delaying the flowering time so as to lengthen the growth period. Hence, Patent Documents (JP Patent Publication (Kohyo) No. 2001-505410 A; JP Patent Publication (Kohyo) No. 2001-519659 A; JP Patent Publication (Kohyo) No. 2007-530063 A; JP Patent Publication (Kokai) No. 2005-130770 A; JP Patent Publication (Kohyo) No. 2000-515020 A; JP Patent Publication (Kohyo) No. 9-503389 A (1997); and JP Patent Publication (Kokai) No. 2005-52114 A) disclose no techniques for achieving the effects of increasing the production of the biomass of an entire plant through application of general culture and/or growth conditions.

DISCLOSURE OF THE INVENTION

Object to be Achieved by the Invention

In view of the above circumstances, an object of the present invention is to search for genes having novel functions of drastically improving the amount of the biomass of an entire plant even under general culture and/or growth conditions and thus to provide a technique with which the production of plant biomass can be drastically increased.

Means to Achieve the Object

As a result of intensive studies to achieve the above object, the present inventors have made the novel finding that the production of plant biomass can be drastically improved by: introducing a gene encoding a receptor-like protein that has a leucine-rich repeat structure and a characteristic domain in a molecule thereof; or modifying an expression control region of an endogenous gene corresponding to the gene. Thus, they have completed the present invention.

Specifically, the plant according to the present invention is a plant into which the AT3G05660 gene encoding a receptor-like protein having a leucine-rich repeat structure or a gene functionally equivalent to such a gene is introduced, or in which an expression control region of an endogenous gene corresponding to the gene is modified.

Also, the method for increasing the production of biomass according to the present invention comprises introducing the AT3G05660 gene encoding a receptor-like protein having a leucine-rich repeat structure or a gene functionally equivalent to the gene, or modifying an expression control region of an endogenous gene corresponding to the gene.

Furthermore, the method for producing a plant according to the present invention comprises the steps of: preparing a transformed plant into which the AT3G05660 gene encoding a receptor-like protein having a leucine-rich repeat structure or a gene functionally equivalent to such a gene is introduced, or in which an expression control region of an endogenous gene corresponding to the gene is modified; and measuring the amounts of biomass of progeny plants of the transformed plant and then selecting a line in which the amount of biomass is significantly improved.

In the present invention, the above gene preferably encodes any one of the following proteins (a) to (c):

(a) a protein comprising the amino acid sequence of SEQ ID NO: 3;

(b) a receptor-like protein comprising an amino acid sequence that has a deletion, a substitution, an addition, or an insertion of one or a plurality of amino acids with respect to the amino acid sequence of SEQ ID NO: 3 and having a leucine-rich repeat structure; and (c) a receptor-like protein that is encoded by a polynucleotide hybridizing under stringent conditions to a polynucleotide comprising a nucleotide sequence complementary to the nucleotide sequence of SEQ ID NO: 2 and has a leucine-rich repeat structure.

Also, in the present invention, an example of the above functionally equivalent gene is a gene encoding a receptor-like protein, which is derived from an organism other than *Arabidopsis thaliana* and has a leucine-rich repeat structure.

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

This description hereby incorporates the entire content of the description and/or the drawings of Japanese Patent Application No. 2008-288869, which is the basis of the priority claim of this application.

Effect of the Invention

The plant according to the present invention is a plant capable of producing significantly improved amount of biomass compared with wild-type plants. Also, the method for increasing the production of biomass according to the present invention can realize the significantly increased production of biomass compared with target wild-type plants. Furthermore, the method for producing a plant according to the present invention makes it possible to produce a plant capable of producing significantly improved amount of biomass compared with wild-type plants. Therefore, through application of the present invention, for example, productivity can be improved when the plant itself is a product and this can be achieved at lower cost.

BRIEF DESCRIPTION OF THE DRAWINGS

FIG. 1 is a characteristic diagram showing the results of alignment analysis using a CLUSTAL W (1.83) multiple sequence alignment program for the amino acid sequences encoded by AT3G05660 (SEQ ID NO: 3) and AT3G05650 (SEQ ID NO: 22).

FIG. 2-1 is a characteristic diagram showing the results of alignment analysis using a CLUSTAL W (1.83) multiple sequence alignment program for the amino acid sequences encoded by AT3G05660 (SEQ ID NO: 3), AT2G33080 (SEQ ID NO: 23), and AT3G05650 (SEQ ID NO: 22).

FIG. 2-2 is a characteristic diagram showing the results of alignment analysis using a CLUSTAL W (1.83) multiple sequence alignment program for the amino acid sequences encoded by AT3G05660 (SEQ ID NO: 3), AT2G33080 (SEQ ID NO: 23), and AT3G05650 (SEQ ID NO: 22).

BEST MODE FOR CARRYING OUT THE INVENTION

Figure 3:
FIG. 3 is a photo showing the aerial parts of wild-type plants and transformed plants into which a fragment containing ORF of AT3G05660 was introduced.

The present invention will be explained in detail as follows.

The plant according to the present invention is a plant into which the AT3G05660 gene encoding a receptor-like protein (hereinafter, abbreviated as LRR-RLP) having a leucine-rich repeat structure or a gene functionally equivalent to such a gene is introduced, or in which an expression control region of an endogenous gene corresponding to the AT3G05660 gene is modified; and the amount of biomass is significantly improved compared with wild-type plants. The expression level of a target gene can be significantly increased compared with that in a wild-type plant by exogenously introducing the target gene or modifying an expression control region of an endogenous gene corresponding to the AT3G05660 gene. The plant according to the present invention may be a plant in which the LRR-RLP gene is expressed in all plant tissues or at least some plant tissues. Here, the term "plant tissue(s)" is meant to include plant organ(s) such as leaves, stems, seeds, roots, and flowers.

Also, the term "expression control region" refers to a promoter region to which RNA polymerase binds and a region to which another transcription factor binds. A transcriptional regulatory region is preferably modified by substituting a promoter region, for example, among endogenous transcriptional regulatory regions with a promoter region that enables a higher expression level.

LRR-RLP Gene

In the present invention, an LRR-RLP gene is the AT3G05660 gene or a gene functionally equivalent to such a gene. In addition, as described in Reference 1 (Plant Physiology, June 2003, Vol. 132, pp. 530-543), LRR-RLP is involved in receptor-like kinase (RLK)-signals and is a protein analogous to an extracellular domain of RLK. LRR-RLP encoded by the AT3G05660 gene comprises a characteristic domain consisting of the amino acid sequence of SEQ ID NO: 1. Hence, when LRR-RLP (AT2G33080 or AT3G05650) having high homology with LRR-RLP encoded by the AT3G05660 gene is compared with AT3G05660 at the amino acid sequence level, it is understood that the amino acid sequence of SEQ ID NO: 1 is specific in AT3G05660.

FIG. 1 shows the results of alignment analysis using a CLUSTAL W (1.83) multiple sequence alignment program (that can be used for DDBJ of the National Institute of Genetics (clustalw.ddbj.nig.ac.jp/top-j.html)) for AT3G05660 and AT3G05650. Also, FIG. 2 shows the results of similar alignment analysis for AT3G05660, AT2G33080, and AT3G05650.

As shown in FIG. 1 and FIG. 2, it is understood that the amino acid sequence of SEQ ID NO: 1 (in FIGS. 1 and 2, denoted as Region A) is a specific domain capable of distinguishing AT3G05660 from AT2G33080 and AT3G05650. Regarding AT3G05660 having a domain consisting of the amino acid sequence of SEQ ID NO: 1, it was revealed in the Examples described later that AT3G05660 has effects of significantly improving the production of biomass. The nucleotide sequence of the coding region of the AT3G05660 gene is of SEQ ID NO: 2. The amino acid sequence of LRR-RLP encoded by the AT3G05660 gene is of SEQ ID NO: 3.

Also, in the present invention, a gene functionally equivalent to the AT3G05660 gene may also be introduced into a plant. Here, the term "functionally equivalent gene" refers to, for example, a gene from an organism other than *Arabidopsis thaliana*, corresponding to the AT3G05660 gene encoding LRR-RLP.

The above genes, which are from organisms other than *Arabidopsis thaliana* and are functionally equivalent to the AT3G05660 gene, are not particularly limited and can be specified by searching for a database containing gene sequences of various organisms. Specifically, DDBJ/EMBL/GenBank International Nucleotide Sequence Database or SWISS-PROT database is searched, for example, using the nucleotide sequence of SEQ ID NO: 2 or the nucleotide sequence of SEQ ID NO: 3 as a query sequence, so that the sequence can be easily searched for and/or identified from such a known database.

In addition, LRR-RLP genes in the present invention are not limited to the above described LRR-RLP genes comprising the nucleotide sequences and the amino acid sequences specified by SEQ ID NOS. Hence, the LRR-RLP gene may be a gene that contains an amino acid sequence having a deletion, a substitution, an addition, or an insertion of one or a plurality of amino acid sequences with respect to the amino acid sequences specified by the above-described SEQ ID NOS, and has activity of functioning as LRR-RLP. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by modifying a nucleotide sequence encoding the above LRR-RLP gene by a technique known in the art. Mutation can be introduced into a nucleotide sequence by a known technique such as the Kunkel method or the Gapped duplex method or a method based thereof. For example, mutation is introduced with a mutagenesis kit using site-directed mutagenesis (e.g., Mutant-K or Mutant-G (both are trade names of Takara Bio)) or the like, or a LA PCR in vitro Mutagenesis series kit (trade name, Takara Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, LRR-RLP genes may be genes homologous to the LRR-RLP genes comprising the nucleotide sequences and the amino acid sequences specified by the above-described SEQ ID NOS. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes analogous to the LRR-RLP genes comprising the nucleotide sequences and the amino acid sequences specified by the above described SEQ ID NOS include genes encoding proteins: having amino acid sequences that have 70% or more, preferably 80% or more, more preferably 90% or more, and most preferably 95% or more similarity to these amino acid sequences; having a common sequence comprising the amino acid sequence of SEQ ID NO: 1; and having LRR-RLP activity. Here, the value of similarity refers to a value that can be found based on default setting using a computer mounted with a BLAST (Basic Local Alignment Search Tool) program and a database containing gene sequence information.

Also, genes analogous to LRR-RLP genes comprising the nucleotide sequences and the amino acid sequences specified by the above SEQ ID NOS can be identified by, when the plant genome information remains unclarified, extracting the genome from a target plant or constructing a cDNA library for a target plant and then isolating a genomic region or cDNA hybridizing under stringent conditions to at least a portion of the LRR-RLP genes comprising the nucleotide sequences and amino acid sequences specified by the above SEQ ID NOS. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3× SSC. Hybridization can be performed by a conventionally known method such as a method described in J. Sambrook et al. Molecular Cloning, A Laboratory Manual, 2nd Ed., Cold Spring Harbor Laboratory (1989).

The plant according to the present invention exerts significantly improved production of biomass compared with wild-type plants, as a result of introduction of the AT3G05660 gene or a gene functionally equivalent to the gene into a plant or modification of an expression control region of an endogenous gene corresponding to the gene. Examples of a technique for introducing the LRR-RLP gene into a plant include a technique for introducing an expression vector in which an exogenous LRR-RLP gene has been arranged under control of a promoter that enables expression within the plant. Examples of a technique for modifying an expression control region of an endogenous gene corresponding to the gene include a technique for modifying a promoter of an endogenous LRR-RLP gene in a target plant.

A preferred example is a technique for introducing an expression vector in which the above LRR-RLP gene is arranged under control of a promoter that enables expression in a target plant.

Expression Vector

An expression vector is constructed to contain a promoter that enables expression within plants and the above described LRR-RLP gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of the LRR-RLP gene in a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylasexoxidase small subunit gene promoter, a napin gene promoter, and an oleosin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can also be used herein. As such a promoter, any conventionally known promoter can be used. When the above described LRR-RLP gene is site-specifically expressed using such a promoter, a plant organ in which the gene is expressed can be more increased than wild-type plant organs.

In addition, an expression vector may further contain other DNA segments in addition to a promoter and the above LRR-RLP gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter, the above LRR-RLP gene, a transcription repressor converting polynucleotide, and if necessary, the above other DNA segments may be introduced in an predetermined order. For example, the above LRR-RLP gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the above LRR-RLP gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G. (1993) In Planta *Agrobacterium*-mediated gene introduction by infiltration of adult *Arabidopsis* plants. C.R. Acad. Sci. Paris Sci. Vie, 316, 1194-1199., or a method described in Zyprian E, Kado Cl, *Agrobacterium*-mediated plant transformation by novel mini-T vectors in conjunction with a high-copy vir region helper plasmid. Plant Molecular Biology, 1990, 15(2), 245-256. can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

Plants into which an expression vector is introduced or in other words, plants required to increase the production of biomass are not particularly limited. Specifically, through expression of the above-described LRR-RLP gene, effects of increasing the production of biomass can be expected for all plants. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana* (*Arabidopsis thaliana*), Aburana (rapeseed) (*Brassica rapa, Brassica napus*), cabbage (*Brassica oleracea* var. *capitata*), rapeseed (*Brassica rapa, Brassica napus*), Natane (rapeseed) (*Brassica rapa, Brassica napus*), napa (*Brassica rapa* var. *pekinensis*), ging-geng-cai (*Brassica rapa* var. *chinensis*), turnip (*Brassica rapa* var. *rapa*), coleseed greens (*Brassica rapa* var. *hakabura*), potherb mustard (*Brassica rapa* var. *lancinifolia*), komatsuna (*Brassica rapa* var. *peruviridis*), pak choi (*Brassica rapa* var. *chinensis*), daikon (*Brassica Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*) and switch grass (*Panicum*), and the like.

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. This is because the costs for biofuel such as bioethanol, biodiesel, biomethanol, bioDME, bioGTL (BTL), and biobutanol can be reduced by increasing the production of biomass using energy crops.

Also, as described above, LRR-RLP genes that can be used in the present invention can be isolated from various plants and used. Such LRR-RLP genes can be appropriately selected and used, depending on the types of target plant required to increase the biomass production. Specifically, when a plant required to increase the biomass production is a monocotyledon, an LRR-RLP gene isolated from a monocotyledon is preferably expressed.

In addition, in the present invention, even when a plant required to increase the biomass production is a monocotyledon, a dicotyledon-derived LRR-RLP gene may be introduced. Specifically, for example, the *Arabidopsis thaliana*-derived LRR-RLP gene (SEQ ID NO: 2) may be introduced into not only dicotyledons, but also a variety of plants that are classified as monocotyledons, so that the gene is expressed.

Other Steps and Methods

After the above transformation, a step of selecting proper transformants from plants can be performed by a conventionally known method. Such selection method is not particularly limited. For example, selection can be made based on drug resistance such as hygromycin resistance. Alternatively, after the growth of transformants, plants are directly weighed or the any organs or tissues thereof are weighed, the weights are compared with those of wild-type plants, and then plants with significantly increased weights thereof may be selected.

Also, progeny plants can be obtained from transformed plants obtained by transformation according to a conventional method. Progeny plants retaining a trait resulting from the introduction of the LRR-RLP gene or a trait resulting from modification of an expression control region of a relevant endogenous LRR-RLP gene are selected based on the amount of biomass. Therefore, a stable plant line capable of producing an increased amount of biomass because of having the above trait can be produced. Also, plant cells or reproductive materials, such as seeds, fruits, stocks, calluses, tubers, cut ears, or lumps, may be obtained from a transformed plant or an offspring plant thereof. A stable plant line capable of producing an increased amount of biomass because of having the above trait can be mass-produced therefrom based on such materials.

In addition, examples of the term "plant(s)" in the present invention include at least any of grown plants, plant cells, plant tissues, calluses, and seeds. Specifically, in the present invention, any forms of plants that can be finally grown to mature plants are regarded as "plants." Also, examples of such plant cells include various forms of plant cells, such as suspended culture cells, protoplasts, and leaf sections. Plants can be obtained through the growth and differentiation of these plant cells. In addition, regeneration of plants from plant cells can be performed using a conventionally known method depending on the type of plant cells.

As explained above, according to the present invention, plants capable of achieving the significantly increased production of biomass per plant compared with wild-type plants can be provided through introduction of the above LRR-RLP gene having a specific domain into a plant or modification of an expression control region of the endogenous LRR-RLP gene. Here, the term "significantly increased production of biomass" refers to a situation in which the total weight of each plant is statistically significantly increased compared with the same of a wild-type plant. In this case, even when some plant tissues become specifically large and the sizes of the other tissues are equivalent to those of a wild-type plant, it is concluded that the production of biomass is increased if the total weight of the entire plant is large.

According to the present invention, the production of biomass is increased. Hence, improvement in productivity can be achieved in both of the following cases: a case in which a purpose is to produce the whole plant; and a case in which a purpose is to produce some plant tissues (e.g., seeds) or components contained in plants. For example, when a purpose is to produce fats and oils contained in plant seeds, the amounts of fats and oils that can be harvested per area under cultivation can be greatly improved. Here, examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the thus produced fats and oils can be broadly used for household uses or industrial uses and can be further used as raw materials for biodiesel fuel. Hence, according to the present invention, the above fats and oils for household uses or industrial uses, biodiesel fuel, and the like can be produced at low cost with the use of plants in which the LPR-RLP gene has been introduced or an expression control region of the endogenous LPR-RLP gene has been modified.

EXAMPLES

The present invention will be specifically described in the following examples. However, the examples are not intended to limit the technical scope of the present invention.

Example 1

1. Materials and Methods 1-1. Experimental Materials

As experimental materials, seeds of *Arabidopsis thaliana* mutants (Activation-tag lines: Weigel T-DNA lines, Total of 20072 lines) were used. In addition, the seeds were purchased from the Nottingham *Arabidopsis* Stock Centre (NASC). Regarding the seeds used as experimental materials, Weigel, D. et al., 2000, Plant Physiol. 122, 1003-1013 can be referred to.

1-2. Methods 1-2-1. Selection of Salt-Resistant Mutants

Seeds of Weigel T-DNA lines were aseptically sowed on 125 mM or 150 mM NaCl-containing modified MS agar (1%) medium [vitamins in B5 medium, 10 g/l sucrose, and 8 g/L agar (for bacterial medium; Wako Pure Chemical Industries, Ltd.)] and then cultured at 22° C. under 30-100 µmol/m$^2$/sec illumination (a cycle of 16 hours in the light/8 hours in the dark). Two to four weeks after sowing, salt-resistant mutant candidates were selected. In addition, regarding MS medium, see Murashige, T. et al., 1962, Physiol. Plant. 15, 473-497. Also, regarding the B5 medium, see Gamborg, O. L. et al., 1968, Experimental Cell Research 50, 151-158.

1-2-2. DNA Preparation

A site for insertion of T-DNA into the genome of the thus selected salt-resistant *Arabidopsis thaliana* line was determined by a TAIL-PCR method. First, young leaves were harvested from the cultivated *Arabidopsis thaliana* plants, and then they were crushed while undergoing liquid nitrogen freezing. DNA was prepared using a DNA preparation kit (DNeasy Plant Mini Kit, QIAGEN) according to the standard protocols included with the kit.

1-2-3. TAIL-PCR Method and Presumption of T-DNA Insertion Site

Three (3) types of specific primer, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Genomics, 25, 674-681, 1995, Plant J., 8, 457-463, 1995) was performed, so that genomic DNA adjacent to T-DNA was amplified.

The specific sequences of the primers TL1, TL2, TL3, and P1 are as follows.

```
                                      (SEQ ID NO: 4)
 TL1: 5'-TGC TTT CGC CAT TAA ATA GCG ACG G-3'

(SEQ ID NO: 5)
 TL2: 5'-CGC TGC GGA CAT CTA CAT TTT TG-3'

(SEQ ID NO: 6)
 TL3: 5'-TCC CGG ACA TGA AGC CAT TTA C-3'

(SEQ ID NO: 7)
 P1:  5'-NGT CGA SWG ANA WGA A-3'
```

In addition, in SEQ ID NO: 7, "n" represents "a," "g," "c," or "t" (location: 1 and 11), "s" represents "g" or "c" (location: 7), and "w" represents "a" or "t" (location: 8 and 13).

The 1st PCR solution composition and reaction conditions are shown in Table 1 and Table 2, respectively.

TABLE 1

| Template (genomic DNA) | 10 ng |
| 10 × PCR buffer (Takara Bio) | 2 µl |
| 2.5 mM dNTPs (Takara Bio) | 1.6 µl |
| 1$^{st}$ specific primer (TL1: SEQ ID NO: 4) | 0.5 pmol |
| Arbitrary primer P1 (SEQ ID NO: 7) | 100 pmol |
| TaKaRa Ex Taq (Takara Bio) | 1.0 unit |
| Total | 20 µl |

TABLE 2

| #1: | 94° C. (30 seconds)/95° C. (30 seconds) |
| #2: | 5 cycles of 94° C. (30 seconds)/65° C. (30 seconds)/72° C. (1 minute) |
| #3: | 1 cycle of 94° C. (30 seconds)/25° C. (1 minute)→raised to 72° C. within 3 minutes/72° C. (3 minutes) |
| #4: | 94° C. (15 seconds)/65° C. (30 seconds)/72° C. (1 minute), 94° C. (15 seconds)/68° C. (30 seconds)/72° C. (1 minute), and 15 cycles of 94° C. (15 seconds)/44° C. (30 seconds)/72° C. (1 minute) |
| #5: | 72° C. (3 minutes) |

The 2$^{nd}$ PCR solution composition and reaction conditions are shown in Table 3 and Table 4, respectively.

TABLE 3

| Template (50-fold dilution of the 1$^{st}$ PCR product) | 1 µl |
| 10 × PCR buffer (Takara Bio) | 2 µl |
| 2.5 mM dNTPs (Takara Bio) | 1.5 µl |
| 2$^{nd}$ specific primer (TL2: SEQ ID NO: 5) | 5 pmol |
| Arbitrary primer P1 (SEQ ID NO: 7) | 100 pmol |
| TaKaRa Ex Taq (Takara Bio) | 0.8 unit |
| Total | 20 µl |

TABLE 4

| #6: | 94° C. (15 seconds)/64° C. (30 seconds)/72° C. (1 minute), 94° C. (15 seconds)/64° C. (30 seconds)/72° C. (1 minute), and 12 cycles of 94° C. (15 seconds)/44° C. (30 seconds)/72° C. (1 minute) |
| #5: | 72° C. (5 minutes) |

The 3rd PCR solution composition and reaction conditions are shown in Table 5 and Table 6, respectively.

TABLE 5

| | |
|---|---|
| Template (50-fold dilution of the 2nd PCR product) | 1 µl |
| 10 × PCR buffer (Takara Bio) | 5 µl |
| 2.5 mM dNTPs (Takara Bio) | 0.5 µl |
| 3rd specific primer (TL3: SEQ ID NO: 6) | 10 pmol |
| Arbitrary primer P1 (SEQ ID NO: 7) | 100 pmol |
| TaKaRa Ex Taq (Takara Bio) | 1.5 unit |
| Total | 50 µl |

TABLE 6

| | |
|---|---|
| #7: | 20 cycles of<br>94° C. (30 seconds)/44° C. (30 seconds)/72° C. (1 minute) |
| #5: | 72° C. (3 minutes) |

Subsequently, the 2nd and the 3rd reaction products were subjected to agarose gel electrophoresis and then the presence or the absence of amplification and the specificity of reaction products were confirmed. Also, the 3rd amplification products were subjected to a sequencing reaction directly using a BigDye Terminator Cycle Sequencing Kit Ver. 3. 1 (Applied Biosystems) and the specific primer TL3. Thus, a nucleotide sequence was determined using an ABI PRISM 3100 Genetic Analyzer (Applied Biosystems).

As a result, 5 types of nucleotide sequence were determined. Specifically, the sequence information of 538 bp, the sequence information of 311 bp, the sequence information of 498 bp, and the sequence information of 633 bp were obtained. The thus obtained types of sequence information are of SEQ ID NOS: 8-11, respectively.

Using the thus obtained sequence information, The *Arabidopsis* Information Resource (TAIR: arabidopsis.org/) was subjected to a BLAST search. Thus, the T-DNA insertion sites were found to be: a portion between the gene of *Arabidopsis thaliana* chromosome 1 [AGI (The *Arabidopsis* Genome Initiative gene code) code: At1g69990] and the gene [AGI (The *Arabidopsis* Genome Initiative gene code) code: At1g70000]; the gene of *Arabidopsis thaliana* chromosome 5 [AGI (The *Arabidopsis* Genome Initiative gene code) code: At5g39400]; the gene of *Arabidopsis thaliana* chromosome 3 [AGI (The *Arabidopsis* Genome Initiative gene code) code: At3g05630]; and the gene of *Arabidopsis thaliana* chromosome 2 [AGI (The *Arabidopsis* Genome Initiative gene code) code: At2g33110].

1-2-4. Prediction of Activated Genes

Activated genes were predicted from the sequence of a presumed open reading frame (ORF) gene existing within a 10-Kb range near each T-DNA insertion site (the portion between At1g69990 and At1g70000, At5g39400, At3g05630, and At2g33110) revealed in 1-2-3.

1-2-5. Preparation of Mutant Containing Predicted Gene Via Introduction

For amplification of fragments containing the ORF regions of the LRR-RLK (leucine-rich repeat receptor-like protein kinase) gene (AT1G69990), the LRR-RLK (leucine-rich repeat receptor-like protein kinase) gene (AT5G39390), the LRR (leucine-rich repeat) protein gene (AT3G05650), the LRR (leucine-rich repeat) protein gene (AT2G33080), and the LRR (leucine-rich repeat) protein gene (AT3G05660), which were predicted as being activated in 1-2-4, a pair of primers was designed and synthesized for each gene based on the sequence information disclosed in TAIR (arabidopsis.org/home.html) (Table 7). In addition, these pairs of primers were designed so that restriction enzyme sites required upon introduction into expression vectors were added to the primers (Table 7).

TABLE 7

| Gene | Forward | Reverse | Restriction enzyme site | |
|---|---|---|---|---|
| AT1G69990 | 5'-ACG CGT CGA CCC ATC ATG AAA ACG ATC TCA ATC TTC TTC GTC-3'<br>(SEQ ID NO: 12) | 5'-TGT ACA TGT ACA AGT GAG AAC GGT AGA TAA GTA AGT GG-3'<br>(SEQ ID NO: 13) | Sal I | BsrG I |
| AT5G39390 | 5'-ACG CGT CGA CCA AAC GAC GTA TCT CAT AAG TCG ACG CA-3'<br>(SEQ ID NO: 14) | 5'-TGT ACA TGT ACA GGA GAA CTT TGA AGA TCA TCG AGA GG-3'<br>(SEQ ID NO: 15) | Sal I | BsrG I |
| AT3G05650 | 5'-ACG CGT CGA CCC ATC ACA CAC ACA TAC ACA CAC-3'<br>(SEQ ID NO: 16) | 5'-TGT ACA TGT ACA CAG CGT AAA TGA AGA ACA CCC CAA ACT GAA C-3'<br>(SEQ ID NO: 17) | Sal I | BsrG I |
| AT2G33080 | 5'-ACG CGT CGA CAT GTC AGG ATC ACA TCT GCG TTT GC-3'<br>(SEQ ID NO: 18) | 5'-TGT ACA TGT ACA TCA GCA CTT GCT CCT GTT CTT CG-3'<br>(SEQ ID NO: 19) | Sal I | BsrG I |
| AT3G05660 | 5'-ACG CGT CGA CGG AGA AGC AAA ACC TCA TAG AAG TCA ATG AGT CTC ATT CC-3'<br>(SEQ ID NO: 20) | 5'-AAG GAA AAA AGC GGC CGC CCG TAC AAC GTT GCT TTC TTC GCC GAC GTC-3'<br>(SEQ ID NO: 21) | Sal I | Not I |

According to the method described in 1-2-2, a template DNA was prepared from wild-type *Arabidopsis thaliana* (Col-0 ecotype). Takara Ex Taq (Takara Bio Inc.), Platinum Pfx DNA Polymerase (Invitrogen), or Phusion High-Fidelity DNA Polymerase (NEW ENGLAND BioLabs: NEB) was used as an enzyme. The primer pairs listed in Table 7 were used as primers. The relevant PCR solution composition and reaction conditions were used according to protocols included with each enzyme. PCR amplification products were subjected to electrophoresis with 2% agarose gel (TAE buffer) and then fragments were stained with ethidium bromide. A gel containing target fragments was excised using a scalpel. Target DNA fragments were eluted and purified using a GFX PCR DNA and GEL Band Purification Kit (Amersham). Adenin was added to the thus obtained DNA fragment using an A-Addition Kit (QIAGEN). The amplified DNA to which adenine had been added was ligated to a TA-Cloning pCR2.1 vector using a TOPO TA Cloning Kit (Invitrogen) and then transformed into competent cells (*E. coli* TOP 10) included with the kit. After transformation, cells were cultured in LB medium supplemented with 50 µl/ml kanamycin and then transformants were selected. Colonies that had appeared were subjected to liquid culture in LB medium supplemented with 50 µl/ml kanamycin. Plasmid DNA was prepared from the thus obtained microorganisms using a Plasmid Mini Kit (QIAGEN).

The thus obtained fragment containing ORF of the LRR-RLK gene (AT1G69990) was cloned into a vector, the thus obtained fragment containing ORF of the LRR-RLK gene (AT5G39390) was cloned into a vector, the thus obtained fragment containing ORF of the LRR (protein gene (AT3G05650) was cloned into a vector, the thus obtained fragment containing ORF of the LRR protein gene (AT2G33080) was cloned into a vector, and the thus obtained fragment containing ORF of the LRR protein gene (AT3G05660) was cloned into a vector, followed by determination of the nucleotide sequences and sequence analysis.

1-2-6. Construction of Plant Expression Vector

A fragment containing ORF of the LRR-RLK gene (AT1G69990), the LRR-RLK gene (AT5G39390), the LRR protein gene (AT3G05650), the LRR protein gene (AT2G33080), or the protein gene (AT3G05660) was inserted into a plant expression vector pBI121 containing an omega sequence from tobacco mosaic virus. Thus, constructs were prepared.

First, the pCR2.1 vector, in which a fragment containing ORF of the LRR-RLK gene (AT1G69990) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 1850 bp containing ORF of the LRR-RLK gene (AT1G69990) and pBI121 containing the omega sequence were each fractioned and purified from the gel using a GFX PCR DNA and GEL Band Purification Kit (Amersham).

For introduction of a fragment containing ORF of the LRR-RLK gene (AT1G69990) using a pBI121 fragment containing the omega sequence as a vector, the vector and the insert were mixed at a ratio of 1:10, followed by an overnight ligation reaction at 16° C. using an equivalent amount of a TaKaRa Ligation kit ver. 2 (Takara Bio Inc.).

The total amount of the reaction solution was added to 100 µl of competent cells (*E. coli* strain DH5a, TOYOBO), so that transformation was performed according to protocols included with the kit. Cells were applied to LB agar medium containing 50 µg/ml kanamycin and then cultured overnight. Colonies that had appeared were subjected to liquid culture in LB medium supplemented with 50 µg/ml kanamycin. Plasmid DNA was prepared from the thus obtained microorganisms using a Plasmid Mini Kit (QIAGEN).

The thus obtained fragment containing ORF of the LRR-RLK gene (AT1G69990) was subcloned into an expression vector, followed by determination of the nucleotide sequences and sequence analysis.

In addition, the LRR-RLK gene (AT5G39390) and the LRR protein gene (AT2G33080) were incorporated into expression vectors according to the above method, except that primers listed in Table 7 were used, followed by determination of the nucleotide sequences and sequence analysis. The LRR protein gene (AT3G05650) was cloned into a TA-Cloning pCR2.1 vector. Then the vector was treated with an restriction enzyme EcoR I, blunt-ended using a DNA Blunting Kit (Takara Bio Inc.), treated with phenol chloroform, and then treated with a restriction enzyme BsrG I. pBI121 containing an omega sequence was treated with a restriction enzyme Sal I, blunt-ended using a DNA Blunting Kit (Takara Bio Inc.), treated with phenol chloroform, and then treated with a restriction enzyme BsrG I. The resultant was incorporated into an expression vector according to the above method, followed by determination of the nucleotide sequence and sequence analysis. The protein gene (AT3G05660) was treated with a restriction enzyme Not I, blunt-ended using a DNA Blunting Kit (Takara Bio Inc.), treated with phenol chloroform, and then treated with a restriction enzyme Sal I. pBI121 containing an omega sequence was treated with a restriction enzyme BsrG I, blunt-ended using a DNA Blunting Kit (Takara Bio Inc.), treated with phenol chloroform, and then treated with a restriction enzyme Sal I. The resultant was incorporated into an expression vector according to the above method, followed by determination of the nucleotide sequences and sequence analysis.

1-2-7. Gene Introduction into *Arabidopsis thaliana* Using *Agrobacterium* Method The plant expression vector constructed in 1-2-6 was introduced into the *Agrobacterium tumefaciens* C58C1 strain by electroporation (Plant Molecular Biology Manual, Second Edition, B. G. Stanton and A. S. Robbert, Kluwer Acdemic Publishers 1994). Subsequently, *Agrobacterium tumefaciens* into which the plant expression vector had been introduced was introduced into wild-type *Arabidopsis thaliana* (ecotype Col-0) by an infiltration method described by Clough et al. (The Plant Journal 16, 735-743, 1998).

Transformants were selected using kanamycin-containing medium. T2 generation plants were produced by self-pollination.

1-2-8. Confirmation of the Phenotype of Transformant
Measurement of Amount of Biomass:

T2 seeds produced in 1-2-7 were each aseptically sowed in MS agar medium containing 50 mg/L kanamycin and 0.5% sucrose. After 2 weeks, the resulting plants were transplanted into pots (each with a diameter of 50 mm) containing vermiculite mixed soil. As control plants, *Arabidopsis* plants that had not undergone recombination and had been aseptically sowed in MS agar medium containing 0.5% sucrose were transplanted. They were cultivated under conditions of 23° C. and 8 hours in the light/16 hours in the dark (short-day conditions) and with a light intensity of about 160 $\mu E/cm^2$ for a total of 6 weeks after transplantation. After cultivation, above-ground parts of the plants were placed in paper bags and dried under conditions of 22° C. and humidity of 60% for 2 weeks. The total amounts of biomass were weighed using an electronic balance.

2. Results

Regarding the results of 1-2-8 (Measurement of amount of biomass), FIG. 3 shows a photo of the above-ground parts of wild-type plants and transformed plants into which a fragment containing ORF of the protein gene (AT3G05660) had been introduced. Also, FIG. 4 shows the results of measuring the total amounts of biomass of the above-ground parts of a wild-type plant, a transformed plant into which the LRR-RLK protein gene (AT1G69990) had been introduced, a transformed plant into which the LRR-RLK protein gene (AT5G39390) had been introduced, a transformed plant into which the LRR protein gene (AT3G05650) had been introduced, a transformed plant into which the LRR protein gene (AT2G33080) had been introduced, and a transformed plant into which the protein gene (AT3G05660) had been introduced.

Figure 4:
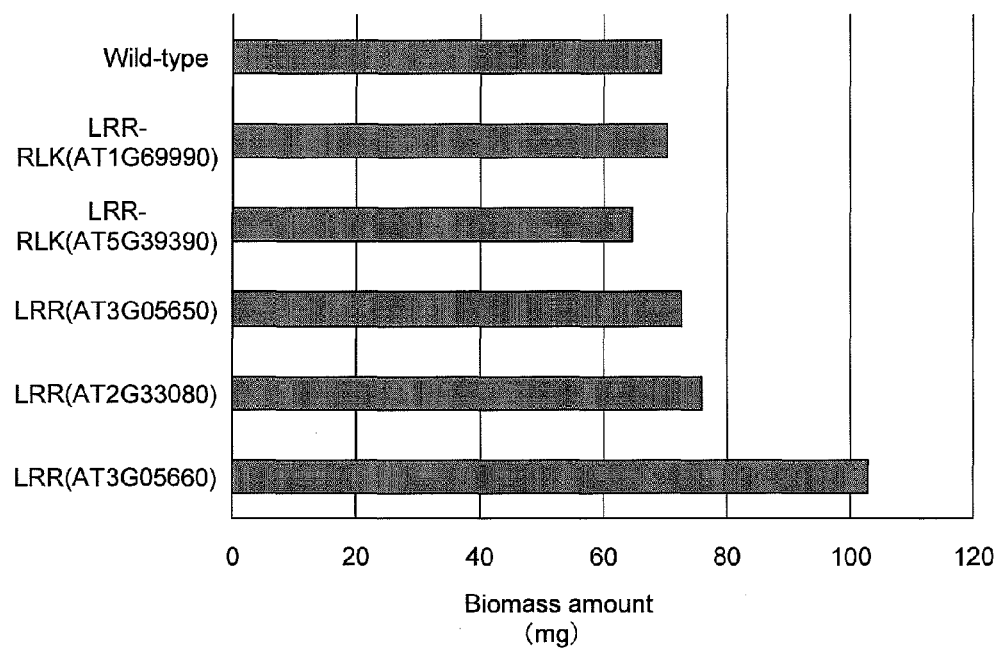
FIG. 4 is a characteristic diagram showing the results of measuring the total amounts of the biomass of the aerial parts of: a wild-type plant; a transformed plant into which the LRR-RLK protein gene (AT1G69990) was introduced; a transformed plant into which the LRR-RLK protein gene (AT5G39390) was introduced; a transformed plant into which the LRR protein gene (AT3G05650) was introduced; a transformed plant into which the LRR protein gene (AT2G33080) was introduced; and a transformed plant into which the protein gene (AT3G05660) was introduced.

As shown in FIGS. 3 and 4, it was revealed that in the case of transformed plants into which the fragment containing ORF of the protein gene (AT3G05660) had been introduced, the total amount of biomass of the above-ground parts was much greater than that of a wild-type plant (by about 1.5 times). Meanwhile, it was revealed that in the case of a transformed plant into which the LRR-RLK gene (AT1G69990), the LRR-RLK gene (AT5G39390), the LRR protein gene (AT3G05650), or the LRR protein gene (AT2G33080) had been introduced, the amount of biomass was almost equivalent to that of a wild-type plant.

Based on the above results, it was revealed that the amounts of biomass would be drastically improved in plants into which the AT3G05660 gene had been introduced.

All publications, patents, and patent applications cited herein are incorporated herein by reference in their entirety.

---

30/30

The invention claimed is:

1. A method for increasing the production of biomass in a plant as compared to a wild-type plant, wherein said method comprises step (i) or (ii):
   (i) introducing, into a plant, a polynucleotide encoding a protein selected from the group consisting of (a) to (b); or (ii) activating an expression control region of an endogenous gene encoding a protein selected from the group consisting of (a) to (b), wherein proteins (a) to (b) are:
   (a) a protein comprising the amino acid sequence of SEQ ID NO: 3; and
   (b) a protein comprising the amino acid sequence of SEQ ID NO: 3 but in which 1-10 amino acids have been deleted, substituted, and/or added in the sequence of SEQ ID NO: 3.

2. The method according to claim 1, wherein said plant is a dicotyledon.

3. The method according to claim 1, wherein said plant is of the family Brassicaceae.

4. The method according to claim 1, wherein said plant is *Arabidopsis thaliana*.

5. A method for selecting a plant with increased production of biomass, wherein said method comprises steps (1) to (3):
   (1) the step of (i) introducing, into a plant, a polynucleotide encoding a protein selected from the group consisting of (a) to (b); or (ii) activating, in a plant, an expression control region of an endogenous gene encoding a protein selected from the group consisting of (a) to (b), wherein proteins (a) to (b) are:
   (a) a protein comprising the amino acid sequence of SEQ ID NO: 3; and
   (b) a protein comprising the amino acid sequence of SEQ ID NO: 3 but in which 1-10 amino acids have been deleted, substituted, and/or added in the sequence of SEQ ID NO: 3;
   (2) measuring the amount of biomass produced by the plant resulting from step (1); and
   (3) selecting the plant resulting from step (1) when the plant exhibits increased production of biomass in comparison with a wild-type plant.

6. The method according to claim 5, wherein said plant is a dicotyledon.

7. The method according to claim 5, wherein said plant is of the family Brassicaceae.

8. The method according to claim 5, wherein said plant is *Arabidopsis thaliana*.

* * * * *

SEQUENCE LISTING

```
<160> NUMBER OF SEQ ID NOS: 23

<210> SEQ ID NO 1
<211> LENGTH: 24
<212> TYPE: PRT
<213> ORGANISM: Artificial Sequence
<220> FEATURE:
<223> OTHER INFORMATION: A characteristic domain in LRR-RLP gene

<400> SEQUENCE: 1

Gly Trp Ile Pro Ser Ser Leu Gly Asn Leu Phe His Leu Thr Ser Leu
1               5                   10                  15

His Leu Tyr Asp Asn Asn Phe Gly
            20

<210> SEQ ID NO 2
<211> LENGTH: 2628
<212> TYPE: DNA
<213> ORGANISM: Arabidopsis thaliana
<220> FEATURE:
<221> NAME/KEY: CDS
<222> LOCATION: (1)..(2628)

<400> SEQUENCE: 2 atg agt ctc att cct att act ttt tat ttt ctc ttc ttg ttc ttt tct        48
Met Ser Leu Ile Pro Ile Thr Phe Tyr Phe Leu Phe Leu Phe Phe Ser
1               5                   10                  15 aat ttt cga ggt gtt ttt gct gtt cct aat ata cac tta tgt cat ttc        96
Asn Phe Arg Gly Val Phe Ala Val Pro Asn Ile His Leu Cys His Phe
            20                  25                  30 gaa caa aga gat gca ctt ctc gag ttc aag aac gag ttt aag att aag       144
Glu Gln Arg Asp Ala Leu Leu Glu Phe Lys Asn Glu Phe Lys Ile Lys
        35                  40                  45 aag cct tgt ttt ggt tgt cca agt cct ctg aag aca aag tca tgg gag       192
Lys Pro Cys Phe Gly Cys Pro Ser Pro Leu Lys Thr Lys Ser Trp Glu
    50                  55                  60 aat ggc agc gac tgt tgt cat tgg gat ggt att act tgc gat gct aag       240
Asn Gly Ser Asp Cys Cys His Trp Asp Gly Ile Thr Cys Asp Ala Lys
65                  70                  75                  80 acc ggg gaa gta atc gag ata gac ctt atg tgc agc tgc ctc cat ggc       288
Thr Gly Glu Val Ile Glu Ile Asp Leu Met Cys Ser Cys Leu His Gly
                85                  90                  95 tgg ttt cat tcc aac agt aat ctt tct atg ctt caa aat ttc cat ttt       336
Trp Phe His Ser Asn Ser Asn Leu Ser Met Leu Gln Asn Phe His Phe
            100                 105                 110
```

```
cta acc act cta gac ctt tca tat aat cat ttg agt ggt caa atc tca      384
Leu Thr Thr Leu Asp Leu Ser Tyr Asn His Leu Ser Gly Gln Ile Ser
        115                 120                 125 tct tct att gga aac ctt tct cat ctc acc act ctc gac ctt tct gga      432
Ser Ser Ile Gly Asn Leu Ser His Leu Thr Thr Leu Asp Leu Ser Gly
130                 135                 140 aat aac ttc agt ggt tgg att cct tct tcc ctt gga aac ctt ttt cac      480
Asn Asn Phe Ser Gly Trp Ile Pro Ser Ser Leu Gly Asn Leu Phe His
145                 150                 155                 160 ctc acc tct ctc cac ctc tat gat aac aat ttt ggt ggt gaa atc cca      528
Leu Thr Ser Leu His Leu Tyr Asp Asn Asn Phe Gly Gly Glu Ile Pro
                165                 170                 175 tct tca ctt gga aat ctg tcg tat ctc acc ttt ctc gac cta tct act      576
Ser Ser Leu Gly Asn Leu Ser Tyr Leu Thr Phe Leu Asp Leu Ser Thr
                180                 185                 190 aac aat ttt gtt ggt gaa atc cct tct tct ttt ggc agt ttg aac caa      624
Asn Asn Phe Val Gly Glu Ile Pro Ser Ser Phe Gly Ser Leu Asn Gln
                195                 200                 205 ttg tct att tta cgt ctt gat aat aat aag ctt agt ggt aac ctc cca      672
Leu Ser Ile Leu Arg Leu Asp Asn Asn Lys Leu Ser Gly Asn Leu Pro
210                 215                 220 ctt gaa gta atc aat ctt aca aag ttg tca gag ata tca ctc tct cac      720
Leu Glu Val Ile Asn Leu Thr Lys Leu Ser Glu Ile Ser Leu Ser His
225                 230                 235                 240 aat cag ttc aca ggc acg ctt cct cct aac atc act cta tcc atc         768
Asn Gln Phe Thr Gly Thr Leu Pro Pro Asn Ile Thr Leu Ser Ile
                245                 250                 255 ttg gag tcc ttt tcg gca agt gga aac aat ttc gtt gga act atc cct      816
Leu Glu Ser Phe Ser Ala Ser Gly Asn Asn Phe Val Gly Thr Ile Pro
                260                 265                 270 tcc tct ctc ttc acc att cct tct ata act ctt att ttt ttg gac aat      864
Ser Ser Leu Phe Thr Ile Pro Ser Ile Thr Leu Ile Phe Leu Asp Asn
            275                 280                 285 aac caa ctc agc ggc act ctt gag ttt ggg aat ata tct tca ccg tct      912
Asn Gln Leu Ser Gly Thr Leu Glu Phe Gly Asn Ile Ser Ser Pro Ser
            290                 295                 300 aat tta cta gtg tta caa ctt ggc ggt aac aac ttg aga ggt cca atc      960
Asn Leu Leu Val Leu Gln Leu Gly Gly Asn Asn Leu Arg Gly Pro Ile
305                 310                 315                 320 cct aca tct att tcc aga tta gtc aac ctt agg aca ctt gac ctt tcc     1008
Pro Thr Ser Ile Ser Arg Leu Val Asn Leu Arg Thr Leu Asp Leu Ser
                325                 330                 335 cat ttc aac atc caa ggc caa gtt gac ttt aat atc ttc tcg cat ctc     1056
His Phe Asn Ile Gln Gly Gln Val Asp Phe Asn Ile Phe Ser His Leu
                340                 345                 350 aag ttg cta gga aac ctt tac cta tcc cat tcc aac acc acc act aca     1104
Lys Leu Leu Gly Asn Leu Tyr Leu Ser His Ser Asn Thr Thr Thr Thr
            355                 360                 365 att gac ttg aat gca gtc tta tca tgt ttc aag atg ctc att tca ttg     1152
Ile Asp Leu Asn Ala Val Leu Ser Cys Phe Lys Met Leu Ile Ser Leu
370                 375                 380 gat ctc tca ggc aac cat gtt tta gtc aca aac aaa agt tca gtt tct     1200
Asp Leu Ser Gly Asn His Val Leu Val Thr Asn Lys Ser Ser Val Ser
385                 390                 395                 400 gac cct cct ttg gga ttg ata ggc tct ttg aac tta tca gga tgc ggt     1248
Asp Pro Pro Leu Gly Leu Ile Gly Ser Leu Asn Leu Ser Gly Cys Gly
                405                 410                 415 atc acc gag ttt cca gat atc cta aga acg caa cgc caa atg agg acg     1296
Ile Thr Glu Phe Pro Asp Ile Leu Arg Thr Gln Arg Gln Met Arg Thr
            420                 425                 430
```

-continued

```
cta gac att tcc aac aac aaa atc aaa ggc caa gtg cct agc tgg tta    1344
Leu Asp Ile Ser Asn Asn Lys Ile Lys Gly Gln Val Pro Ser Trp Leu
        435                 440                 445 cta tta cag ttg gag tac atg cat atc tcc aac aac aat ttc atc ggt    1392
Leu Leu Gln Leu Glu Tyr Met His Ile Ser Asn Asn Asn Phe Ile Gly
    450                 455                 460 ttc gaa aga tca acg aaa ctt gaa aaa acc gta gtc cca aaa cca tct    1440
Phe Glu Arg Ser Thr Lys Leu Glu Lys Thr Val Val Pro Lys Pro Ser
465                 470                 475                 480 atg aag cac ttt ttt ggc tcc aat aac aat ttc agt gga aag att cca    1488
Met Lys His Phe Phe Gly Ser Asn Asn Asn Phe Ser Gly Lys Ile Pro
                485                 490                 495 tct ttc ata tgc tcg ttg cgc tct cta atc att ctc gat tta tct aac    1536
Ser Phe Ile Cys Ser Leu Arg Ser Leu Ile Ile Leu Asp Leu Ser Asn
            500                 505                 510 aac aac ttc agt ggt gca atc cct cct tgt gtg gga aaa ttc aag agt    1584
Asn Asn Phe Ser Gly Ala Ile Pro Pro Cys Val Gly Lys Phe Lys Ser
        515                 520                 525 act ctt tca gat ctt aac cta cgt cgg aat cgt ctt agt gga agt ctt    1632
Thr Leu Ser Asp Leu Asn Leu Arg Arg Asn Arg Leu Ser Gly Ser Leu
    530                 535                 540 cca aag act ata ata aaa agt tta agg tct ctt gat gtg agt cat aac    1680
Pro Lys Thr Ile Ile Lys Ser Leu Arg Ser Leu Asp Val Ser His Asn
545                 550                 555                 560 gaa ctg gag gga aag ctt cca aga tct ttg atc cac ttc tct act ctt    1728
Glu Leu Glu Gly Lys Leu Pro Arg Ser Leu Ile His Phe Ser Thr Leu
                565                 570                 575 gaa gtt ttg aat gta gaa agc aac aga atc aac gac acg ttt ccg ttc    1776
Glu Val Leu Asn Val Glu Ser Asn Arg Ile Asn Asp Thr Phe Pro Phe
            580                 585                 590 tgg ttg agt tct cta aaa aag ctg caa gtt ctt gtc tta cgc tcc aac    1824
Trp Leu Ser Ser Leu Lys Lys Leu Gln Val Leu Val Leu Arg Ser Asn
        595                 600                 605 gca ttt cac gga cgg ata cac aag act cgg ttt cct aag ttg cga atc    1872
Ala Phe His Gly Arg Ile His Lys Thr Arg Phe Pro Lys Leu Arg Ile
    610                 615                 620 atc gac ata tcc cgt aat cac ttc aat ggg aca ttg cca tca gat tgc    1920
Ile Asp Ile Ser Arg Asn His Phe Asn Gly Thr Leu Pro Ser Asp Cys
625                 630                 635                 640 ttt gtg gag tgg act ggg atg cac tca ctt gaa aaa aat gaa gat cgg    1968
Phe Val Glu Trp Thr Gly Met His Ser Leu Glu Lys Asn Glu Asp Arg
                645                 650                 655 ttt aac gaa aag tac atg gga tca ggc tat tac cat gat tca atg gtt    2016
Phe Asn Glu Lys Tyr Met Gly Ser Gly Tyr Tyr His Asp Ser Met Val
            660                 665                 670 ctg atg aat aaa ggc tta gag atg gag ctg gta cgt atc cta aaa atc    2064
Leu Met Asn Lys Gly Leu Glu Met Glu Leu Val Arg Ile Leu Lys Ile
        675                 680                 685 tat aca gct ctc gac ttc tct gga aac aaa ttt gaa gga gag att cca    2112
Tyr Thr Ala Leu Asp Phe Ser Gly Asn Lys Phe Glu Gly Glu Ile Pro
    690                 695                 700 aga tcc atc ggt cta ttg aaa gaa ctt cat atc ctc aac ttg tca agc    2160
Arg Ser Ile Gly Leu Leu Lys Glu Leu His Ile Leu Asn Leu Ser Ser
705                 710                 715                 720 aat ggt ttc acc ggc cac atc cca tca tct atg ggg aac ctg aga gag    2208
Asn Gly Phe Thr Gly His Ile Pro Ser Ser Met Gly Asn Leu Arg Glu
                725                 730                 735 ctc gag tca ctg gat gtt tcc cga aac aag ctt tca gga gaa att cca    2256
Leu Glu Ser Leu Asp Val Ser Arg Asn Lys Leu Ser Gly Glu Ile Pro
```

```
                    740                 745                 750
caa gaa cta ggg aac ctc tcg tac ctt gcg tac atg aac ttt tct cat      2304
Gln Glu Leu Gly Asn Leu Ser Tyr Leu Ala Tyr Met Asn Phe Ser His
        755                 760                 765 aac cag ctt gtc ggt caa gta cca gga ggc acc cag ttt cga acg caa      2352
Asn Gln Leu Val Gly Gln Val Pro Gly Gly Thr Gln Phe Arg Thr Gln
770                 775                 780 tcc gct tcg tct ttt gaa gaa aac ctt gga ctt tgt ggt cgt cct ctc      2400
Ser Ala Ser Ser Phe Glu Glu Asn Leu Gly Leu Cys Gly Arg Pro Leu
785                 790                 795                 800 gaa gaa tgt aga gtt gtc cat gag ccg acg cct tca ggg gaa tca gaa      2448
Glu Glu Cys Arg Val Val His Glu Pro Thr Pro Ser Gly Glu Ser Glu
                    805                 810                 815 aca ttg gaa tca gaa caa gtc ttg agt tgg att gca gct gcc ata ggg      2496
Thr Leu Glu Ser Glu Gln Val Leu Ser Trp Ile Ala Ala Ala Ile Gly
        820                 825                 830 ttc aca cct ggt atc gtg ctt gga ttg acc att ggg cac atc gtg ctt      2544
Phe Thr Pro Gly Ile Val Leu Gly Leu Thr Ile Gly His Ile Val Leu
835                 840                 845 tcc tcc aaa ccg cgt tgg ttc ttc aag gtg ttg tac atc aac aac agt      2592
Ser Ser Lys Pro Arg Trp Phe Phe Lys Val Leu Tyr Ile Asn Asn Ser
850                 855                 860 cgt aga cgc aga cga act cgt tct gag aaa tcc taa                      2628
Arg Arg Arg Arg Arg Thr Arg Ser Glu Lys Ser
865                 870                 875

<210> SEQ ID NO 3
<211> LENGTH: 875
<212> TYPE: PRT
<213> ORGANISM: Arabidopsis thaliana

<400> SEQUENCE: 3

Met Ser Leu Ile Pro Ile Thr Phe Tyr Phe Leu Phe Leu Phe Phe Ser
1               5                   10                  15

Asn Phe Arg Gly Val Phe Ala Val Pro Asn Ile His Leu Cys His Phe
            20                  25                  30

Glu Gln Arg Asp Ala Leu Leu Glu Phe Lys Asn Glu Phe Lys Ile Lys
        35                  40                  45

Lys Pro Cys Phe Gly Cys Pro Ser Pro Leu Lys Thr Lys Ser Trp Glu
    50                  55                  60

Asn Gly Ser Asp Cys Cys His Trp Asp Gly Ile Thr Cys Asp Ala Lys
65                  70                  75                  80

Thr Gly Glu Val Ile Glu Ile Asp Leu Met Cys Ser Cys Leu His Gly
                85                  90                  95

Trp Phe His Ser Asn Ser Asn Leu Ser Met Leu Gln Asn Phe His Phe
            100                 105                 110

Leu Thr Thr Leu Asp Leu Ser Tyr Asn His Leu Ser Gly Gln Ile Ser
        115                 120                 125

Ser Ser Ile Gly Asn Leu Ser His Leu Thr Thr Leu Asp Leu Ser Gly
    130                 135                 140

Asn Asn Phe Ser Gly Trp Ile Pro Ser Ser Leu Gly Asn Leu Phe His
145                 150                 155                 160

Leu Thr Ser Leu His Leu Tyr Asp Asn Asn Phe Gly Gly Glu Ile Pro
                165                 170                 175

Ser Ser Leu Gly Asn Leu Ser Tyr Leu Thr Phe Leu Asp Leu Ser Thr
            180                 185                 190

Asn Asn Phe Val Gly Glu Ile Pro Ser Ser Phe Gly Ser Leu Asn Gln
```

```
            195                 200                 205
Leu Ser Ile Leu Arg Leu Asp Asn Asn Lys Leu Ser Gly Asn Leu Pro
210                 215                 220

Leu Glu Val Ile Asn Leu Thr Lys Leu Ser Glu Ile Ser Leu Ser His
225                 230                 235                 240

Asn Gln Phe Thr Gly Thr Leu Pro Pro Asn Ile Thr Ser Leu Ser Ile
                245                 250                 255

Leu Glu Ser Phe Ser Ala Ser Gly Asn Asn Phe Val Gly Thr Ile Pro
            260                 265                 270

Ser Ser Leu Phe Thr Ile Pro Ser Ile Thr Leu Ile Phe Leu Asp Asn
        275                 280                 285

Asn Gln Leu Ser Gly Thr Leu Glu Phe Gly Asn Ile Ser Ser Pro Ser
    290                 295                 300

Asn Leu Leu Val Leu Gln Leu Gly Gly Asn Asn Leu Arg Gly Pro Ile
305                 310                 315                 320

Pro Thr Ser Ile Ser Arg Leu Val Asn Leu Arg Thr Leu Asp Leu Ser
                325                 330                 335

His Phe Asn Ile Gln Gly Gln Val Asp Phe Asn Ile Phe Ser His Leu
            340                 345                 350

Lys Leu Leu Gly Asn Leu Tyr Leu Ser His Ser Asn Thr Thr Thr Thr
        355                 360                 365

Ile Asp Leu Asn Ala Val Leu Ser Cys Phe Lys Met Leu Ile Ser Leu
    370                 375                 380

Asp Leu Ser Gly Asn His Val Leu Val Thr Asn Lys Ser Ser Val Ser
385                 390                 395                 400

Asp Pro Pro Leu Gly Leu Ile Gly Ser Leu Asn Leu Ser Gly Cys Gly
                405                 410                 415

Ile Thr Glu Phe Pro Asp Ile Leu Arg Thr Gln Arg Gln Met Arg Thr
            420                 425                 430

Leu Asp Ile Ser Asn Asn Lys Ile Lys Gly Gln Val Pro Ser Trp Leu
        435                 440                 445

Leu Leu Gln Leu Glu Tyr Met His Ile Ser Asn Asn Asn Phe Ile Gly
    450                 455                 460

Phe Glu Arg Ser Thr Lys Leu Glu Lys Thr Val Val Pro Lys Pro Ser
465                 470                 475                 480

Met Lys His Phe Phe Gly Ser Asn Asn Asn Phe Ser Gly Lys Ile Pro
                485                 490                 495

Ser Phe Ile Cys Ser Leu Arg Ser Leu Ile Ile Leu Asp Leu Ser Asn
            500                 505                 510

Asn Asn Phe Ser Gly Ala Ile Pro Pro Cys Val Gly Lys Phe Lys Ser
        515                 520                 525

Thr Leu Ser Asp Leu Asn Leu Arg Arg Asn Arg Leu Ser Gly Ser Leu
    530                 535                 540

Pro Lys Thr Ile Ile Lys Ser Leu Arg Ser Leu Asp Val Ser His Asn
545                 550                 555                 560

Glu Leu Glu Gly Lys Leu Pro Arg Ser Leu Ile His Phe Ser Thr Leu
                565                 570                 575

Glu Val Leu Asn Val Glu Ser Asn Arg Ile Asn Asp Thr Phe Pro Phe
            580                 585                 590

Trp Leu Ser Ser Leu Lys Lys Leu Gln Val Leu Val Leu Arg Ser Asn
        595                 600                 605

Ala Phe His Gly Arg Ile His Lys Thr Arg Phe Pro Lys Leu Arg Ile
    610                 615                 620
```

-continued

Ile Asp Ile Ser Arg Asn His Phe Asn Gly Thr Leu Pro Ser Asp Cys
625                 630                 635                 640

Phe Val Glu Trp Thr Gly Met His Ser Leu Glu Lys Asn Glu Asp Arg
            645                 650                 655

Phe Asn Glu Lys Tyr Met Gly Ser Gly Tyr Tyr His Asp Ser Met Val
        660                 665                 670

Leu Met Asn Lys Gly Leu Glu Met Glu Leu Val Arg Ile Leu Lys Ile
            675                 680                 685

Tyr Thr Ala Leu Asp Phe Ser Gly Asn Lys Phe Glu Gly Glu Ile Pro
690                 695                 700

Arg Ser Ile Gly Leu Leu Lys Glu Leu His Ile Leu Asn Leu Ser Ser
705                 710                 715                 720

Asn Gly Phe Thr Gly His Ile Pro Ser Ser Met Gly Asn Leu Arg Glu
            725                 730                 735

Leu Glu Ser Leu Asp Val Ser Arg Asn Lys Leu Ser Gly Glu Ile Pro
            740                 745                 750

Gln Glu Leu Gly Asn Leu Ser Tyr Leu Ala Tyr Met Asn Phe Ser His
            755                 760                 765

Asn Gln Leu Val Gly Gln Val Pro Gly Gly Thr Gln Phe Arg Thr Gln
770                 775                 780

Ser Ala Ser Ser Phe Glu Glu Asn Leu Gly Leu Cys Gly Arg Pro Leu
785                 790                 795                 800

Glu Glu Cys Arg Val Val His Glu Pro Thr Pro Ser Gly Glu Ser Glu
            805                 810                 815

Thr Leu Glu Ser Glu Gln Val Leu Ser Trp Ile Ala Ala Ala Ile Gly
            820                 825                 830

Phe Thr Pro Gly Ile Val Leu Gly Leu Thr Ile Gly His Ile Val Leu
            835                 840                 845

Ser Ser Lys Pro Arg Trp Phe Phe Lys Val Leu Tyr Ile Asn Asn Ser
850                 855                 860

Arg Arg Arg Arg Arg Thr Arg Ser Glu Lys Ser
865                 870                 875

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
tgctttcgcc attaaatagc gacgg                                      25

<210> SEQ ID NO 5
<211> LENGTH: 23
<212> TYPE: DNA
<213> ORGANISM: Artificial Sequence
<220> FEATURE:
<223> OTHER INFORMATION: Synthetic DNA

<400> SEQUENCE: 5
cgctgcggac atctacattt ttg                                        23

<210> SEQ ID NO 6
<211> LENGTH: 22
<212> TYPE: DNA
<213> ORGANISM: Artificial Sequence
<220> FEATURE:

<223> OTHER INFORMATION: Synthetic DNA

<400> SEQUENCE: 6
tcccggacat gaagccattt ac                                                22

<210> SEQ ID NO 7
<211> LENGTH: 16
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 7
ngtcgaswga nawgaa                                                       16

<210> SEQ ID NO 8
<211> LENGTH: 538
<212> TYPE: DNA
<213> ORGANISM: Arabidopsis thaliana

<400> SEQUENCE: 8
cgatgcttgt ccatatccaa acatttcagc catttagtgc tctcactaaa catcttttaa        60
caaaatatga aataacattc ccaaaattgc gatcaaaagg ctagaaacat cttcaacaat       120
tatgacagtc ctaaaccaac agttcaaaca cgttttatat ctgtttggcc aaattaaacg       180
aatataacat aaaaatacga ttgatcttag acaattacta aagtttctaa ataataatct       240
atactttcac aaaacaagaa atacaaattg attcttgcgc agaaagtgct tggtaccta        300 cttttttac caccttttcct tttcaattga gacatcaaca cattcactaa aacaaactct       360
caaactgctc taaacgacac cgtttagtta cagataactt tacttgtatt taaagtcacc       420
aaaagtttga atttttattt gtgccttcca caaagcttta agcttaaaca cagtcaatgg       480
ccgtccttcc gccataaaag gacaaaaaaa agcttccct cttttcacaa aaccctaa         538

<210> SEQ ID NO 9
<211> LENGTH: 311
<212> TYPE: DNA
<213> ORGANISM: Arabidopsis thaliana
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 9
gaatcctgtc cgtctgttaa ccacatttta taatagttcc attatcgacg aaaaaacntg        60
tcttgattnc tactttgaca aacctgtgag agtaagtcac aaaacaaata ttcttcagac       120 aatgttttg ataagatttt gataagcata tgattcttgg acaggttagt ggtgacatac        180
gcatcacatt ctaccagaaa atgattggaa gccgcctttt ttatacttgc ttcaacacag       240
cttttataac caatggctta cttcaggtaa agaattctcc agatgcctca aactcattct       300
tctcactcga c                                                            311

```
<210> SEQ ID NO 10
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 10
taaccttacg ctttgctcgg tcccagacgc aagattacat ctctttctat ggnttgagat      60
cgnacggacg gctgtttgag gacggtccaa ttgccactag ccagatttac gtgcatagca     120
agttaatgat tgttgatgac cggatcgcag tgatcggatc ttctaatata aacgatagga     180
gcttactagg ttcacgagac tctgaggtac tttcaaaaat ccaattcatt ctttattgca     240
gcaaaacaga gttatgtatt catttgaatc aatcatgttt cagatcggtg ttgtgattga     300
agacaaagaa ttcgtggaat cttcgatgaa cggaatgaag tggatggccg ggaagttctc     360
ttacagtctt agatgttcct tgtggtcaga gcatctcggc cttcacgccg gagaggtaat     420
tttaaaaaat ttctagaaac gcctactact atacatttt gacttcagaa acctttattt      480
tcatctcact cgaccaaa                                                   498

<210> SEQ ID NO 11
<211> LENGTH: 633
<212> TYPE: DNA
<213> ORGANISM: Arabidopsis thaliana
<220> FEATURE:
<221> NAME/KEY: misc_feature
<222> LOCATION: (56)..(57)
<223> OTHER INFORMATION: n is a, c, g, or t

<400> SEQUENCE: 11
tctttggtct gttgatgaga ctctagttgc ggattgcagt gaggtataag catagnncca      60
cagccggtta atattaaatg gagatgaata tgtaattaac acggtttcgt ctgaccgatt     120
caccagagtc tccggttagt tcattaaggg tttgctcaaa cgctttctcc tctgcttccc     180
taatttcgga aacattcgcc tgattttctg agatttttgga atttcttcga attgattgcc    240
atgctgagct caagatttcg actgctgaaa tcgaggcgac ttgcggagcc acctccggct     300
gatgtcgcgg ttatgtgtat ttgcaggaaa tgaaagtgat ctccttattg cggcaaatca     360
gccacttcct gtcgactaaa actgtggtgc agcatgtaag aacaaatgca agttcggaca     420
aacgtgttgt cttggtcagt ggttttactt ggcttagtct tcgattctct acgcgtttca     480
gcgtcaagtt ttctagatct ctaaagcttt cgtgctcgcc gatataaatc tctaatatcg     540
gtcccgtaag atcgaattag attcgcgtcg ttttttaagg aaccaaaata atggcgcaac     600
aatcgttgtt ctacagtttc atcctcactc gac                                 633

<210> SEQ ID NO 12
<211> LENGTH: 42
<212> TYPE: DNA
<213> ORGANISM: Artificial Sequence
<220> FEATURE:
<223> OTHER INFORMATION: Synthetic DNA

<400> SEQUENCE: 12
```
acgcgtcgac ccatcatgaa aacgatctca atcttcttcg tc          42

<210> SEQ ID NO 13
<211> LENGTH: 38
<212> TYPE: DNA
<213> ORGANISM: Artificial Sequence
<220> FEATURE:
<223> OTHER INFORMATION: Synthetic DNA

<400> SEQUENCE: 13
tgtacatgta caagtgagaa cggtagataa gtaagtgg              38

<210> SEQ ID NO 14
<211> LENGTH: 38
<212> TYPE: DNA
<213> ORGANISM: Artificial Sequence
<220> FEATURE:
<223> OTHER INFORMATION: Synthetic DNA

<400> SEQUENCE: 14
acgcgtcgac caaacgacgt atctcataag tcgacgca              38

<210> SEQ ID NO 15
<211> LENGTH: 38
<212> TYPE: DNA
<213> ORGANISM: Artificial Sequence
<220> FEATURE:
<223> OTHER INFORMATION: Synthetic DNA

<400> SEQUENCE: 15
tgtacatgta caggagaact ttgaagatca tcgagagg              38

<210> SEQ ID NO 16
<211> LENGTH: 33
<212> TYPE: DNA
<213> ORGANISM: Artificial Sequence
<220> FEATURE:
<223> OTHER INFORMATION: Synthetic DNA

<400> SEQUENCE: 16
acgcgtcgac ccatcacaca cacatacaca cac                   33

<210> SEQ ID NO 17
<211> LENGTH: 43
<212> TYPE: DNA
<213> ORGANISM: Artificial Sequence
<220> FEATURE:
<223> OTHER INFORMATION: Synthetic DNA

<400> SEQUENCE: 17
tgtacatgta cacagcgtaa atgaagaaca ccccaaactg aac        43

<210> SEQ ID NO 18
<211> LENGTH: 35
<212> TYPE: DNA
<213> ORGANISM: Artificial Sequence
<220> FEATURE:
<223> OTHER INFORMATION: Synthetic DNA

<400> SEQUENCE: 18
acgcgtcgac atgtcaggat cacatctgcg tttgc                 35

<210> SEQ ID NO 19
<211> LENGTH: 35
<212> TYPE: DNA
<213> ORGANISM: Artificial Sequence
<220> FEATURE:
<223> OTHER INFORMATION: Synthetic DNA

<400> SEQUENCE: 19
tgtacatgta catcagcact tgctcctgtt cttcg                35

<210> SEQ ID NO 20
<211> LENGTH: 50
<212> TYPE: DNA
<213> ORGANISM: Artificial Sequence
<220> FEATURE:
<223> OTHER INFORMATION: Synthetic DNA

<400> SEQUENCE: 20
acgcgtcgac ggagaagcaa aacctcatag aagtcaatga gtctcattcc            50

<210> SEQ ID NO 21
<211> LENGTH: 48
<212> TYPE: DNA
<213> ORGANISM: Artificial Sequence
<220> FEATURE:
<223> OTHER INFORMATION: Synthetic DNA

<400> SEQUENCE: 21
aaggaaaaaa gcggccgccc gtacaacgtt gctttcttcg ccgacgtc              48

<210> SEQ ID NO 22
<211> LENGTH: 868
<212> TYPE: PRT
<213> ORGANISM: Arabidopsis thaliana

<400> SEQUENCE: 22

Met Lys Asp Ser Trp Asn Ser Thr Ser Ile Ile Pro Phe Thr Phe Ser
1               5                   10                  15

Ser Leu Ile Phe Phe Leu Phe Thr Phe Asp Phe Gln Asp Val Phe Gly
                20                  25                  30

Val Pro Thr Lys His Leu Cys Arg Leu Glu Gln Arg Asp Ala Leu Leu
            35                  40                  45

Glu Leu Lys Lys Glu Phe Lys Ile Lys Lys Pro Cys Phe Asp Gly Leu
        50                  55                  60

His Pro Thr Thr Glu Ser Trp Ala Asn Asn Ser Asp Cys Cys Tyr Trp
65                  70                  75                  80

Asp Gly Ile Thr Cys Asn Asp Lys Ser Gly Glu Val Leu Glu Leu Asp
                85                  90                  95

Leu Ser Arg Ser Cys Leu Gln Ser Arg Phe His Ser Asn Ser Ser Leu
            100                 105                 110

Phe Thr Val Leu Asn Leu Arg Phe Leu Thr Thr Leu Asp Leu Ser Tyr
        115                 120                 125

Asn Tyr Phe Ser Gly Gln Ile Pro Ser Cys Ile Glu Asn Phe Ser His
    130                 135                 140

Leu Thr Thr Leu Asp Leu Ser Lys Asn Tyr Phe Ser Gly Gly Ile Pro
145                 150                 155                 160

Ser Ser Ile Gly Asn Leu Ser Gln Leu Thr Phe Leu Asp Leu Ser Gly
                165                 170                 175

Asn Glu Phe Val Gly Glu Met Pro Phe Phe Gly Asn Met Asn Gln Leu
            180                 185                 190

Thr Asn Leu Tyr Val Asp Ser Asn Asp Leu Thr Gly Ile Phe Pro Leu
        195                 200                 205

Ser Leu Leu Asn Leu Lys His Leu Ser Asp Leu Ser Leu Ser Arg Asn

```
               210                 215                 220
Gln Phe Thr Gly Thr Leu Pro Ser Asn Met Ser Ser Leu Ser Asn Leu
225                 230                 235                 240

Glu Tyr Phe Glu Ala Trp Gly Asn Ala Phe Thr Gly Thr Leu Pro Ser
                    245                 250                 255

Ser Leu Phe Thr Ile Ala Ser Leu Thr Ser Ile Asn Leu Arg Asn Asn
                260                 265                 270

Gln Leu Asn Gly Thr Leu Glu Phe Gly Asn Ile Ser Ser Pro Ser Thr
                275                 280                 285

Leu Thr Val Leu Asp Ile Ser Asn Asn Asn Phe Ile Gly Pro Ile Pro
            290                 295                 300

Lys Ser Ile Ser Lys Phe Ile Asn Leu Gln Asp Leu Asp Leu Ser His
305                 310                 315                 320

Leu Asn Thr Gln Gly Pro Val Asp Phe Ser Ile Phe Thr Asn Leu Lys
                325                 330                 335

Ser Leu Gln Leu Leu Asn Leu Ser His Leu Asn Thr Thr Thr Thr Ile
                340                 345                 350

Asp Leu Asn Ala Leu Phe Ser Ser His Leu Asn Ser Ile Tyr Ser Met
            355                 360                 365

Asp Leu Ser Gly Asn His Val Ser Ala Thr Thr Lys Ile Ser Val Ala
        370                 375                 380

Asp His His Pro Thr Gln Leu Ile Ser Gln Leu Tyr Leu Ser Gly Cys
385                 390                 395                 400

Gly Ile Thr Glu Phe Pro Glu Leu Leu Arg Ser Gln His Lys Met Thr
                405                 410                 415

Asn Leu Asp Ile Ser Asn Asn Lys Ile Lys Gly Gln Val Pro Gly Trp
                420                 425                 430

Leu Trp Thr Leu Pro Lys Leu Ile Phe Val Asp Leu Ser Asn Asn Ile
            435                 440                 445

Phe Thr Gly Phe Glu Arg Ser Thr Glu His Gly Leu Ser Leu Ile Thr
        450                 455                 460

Lys Pro Ser Met Gln Tyr Leu Val Gly Ser Asn Asn Asn Phe Thr Gly
465                 470                 475                 480

Lys Ile Pro Ser Phe Ile Cys Ala Leu Arg Ser Leu Ile Thr Leu Asp
                485                 490                 495

Leu Ser Asp Asn Asn Leu Asn Gly Ser Ile Pro Pro Cys Met Gly Asn
                500                 505                 510

Leu Lys Ser Thr Leu Ser Phe Leu Asn Leu Arg Gln Asn Arg Leu Gly
            515                 520                 525

Gly Gly Leu Pro Arg Ser Ile Phe Lys Ser Leu Arg Ser Leu Asp Val
        530                 535                 540

Gly His Asn Gln Leu Val Gly Lys Leu Pro Arg Ser Phe Ile Arg Leu
545                 550                 555                 560

Ser Ala Leu Glu Val Leu Asn Val Glu Asn Asn Arg Ile Asn Asp Thr
                565                 570                 575

Phe Pro Phe Trp Leu Ser Ser Leu Lys Lys Leu Gln Val Leu Val Leu
                580                 585                 590

Arg Ser Asn Ala Phe His Gly Pro Ile His His Ala Ser Phe His Thr
            595                 600                 605

Leu Arg Ile Ile Asn Leu Ser His Asn Gln Phe Ser Gly Thr Leu Pro
        610                 615                 620

Ala Asn Tyr Phe Val Asn Trp Asn Ala Met Ser Ser Leu Met Ala Thr
625                 630                 635                 640
```

Glu Asp Arg Ser Gln Glu Lys Tyr Met Gly Asp Ser Phe Arg Tyr Tyr
            645                 650                 655

His Asp Ser Val Val Leu Met Asn Lys Gly Leu Glu Met Glu Leu Val
            660                 665                 670

Arg Ile Leu Lys Ile Tyr Thr Ala Leu Asp Phe Ser Glu Asn Lys Leu
            675                 680                 685

Glu Gly Glu Ile Pro Arg Ser Ile Gly Leu Leu Lys Glu Leu His Val
        690                 695                 700

Leu Asn Leu Ser Ser Asn Ala Phe Thr Gly His Ile Pro Ser Ser Met
705                 710                 715                 720

Gly Asn Leu Arg Glu Leu Glu Ser Leu Asp Val Ser Gln Asn Lys Leu
            725                 730                 735

Ser Gly Glu Ile Pro Gln Glu Leu Gly Asn Leu Ser Tyr Leu Ala Tyr
            740                 745                 750

Met Asn Phe Ser His Asn Gln Leu Gly Gly Leu Val Pro Gly Gly Thr
            755                 760                 765

Gln Phe Arg Arg Gln Asn Cys Ser Ser Phe Lys Asp Asn Pro Gly Leu
        770                 775                 780

Tyr Gly Ser Ser Leu Glu Glu Val Cys Leu Asp Ile His Ala Pro Ala
785                 790                 795                 800

Pro Gln Gln His Glu Pro Pro Glu Leu Glu Glu Asp Arg Glu Val
            805                 810                 815

Phe Ser Trp Ile Ala Ala Ala Ile Gly Phe Gly Pro Gly Ile Ala Phe
            820                 825                 830

Gly Leu Thr Ile Arg Tyr Ile Leu Val Phe Tyr Lys Pro Asp Trp Phe
            835                 840                 845

Met His Thr Phe Gly His Leu Gln Pro Ser Ala His Glu Lys Arg Leu
        850                 855                 860

Arg Arg Lys Gln
865

<210> SEQ ID NO 23
<211> LENGTH: 740
<212> TYPE: PRT
<213> ORGANISM: Arabidopsis thaliana

<400> SEQUENCE: 23

Met Ser Gly Ser His Leu Arg Leu Arg Phe Leu Ser Leu Leu Leu Leu
1               5                   10                  15

Cys Cys Val Ser Ser Thr Ser Ser Leu Phe Thr Phe Ser Tyr Pro
            20                  25                  30

Val Leu Asp Leu Val Ala Cys Arg Ser His Gln Ile Gln Ala Phe Thr
        35                  40                  45

Gln Phe Lys Asn Glu Phe Asp Thr His Arg Cys Asn His Ser Asp His
    50                  55                  60

Ser Asn Gly Val Trp Cys Asp Asn Ser Thr Gly Val Val Thr Lys Leu
65                  70                  75                  80

Gln Leu Asn Ala Cys Leu Ser Gly Thr Leu Asn Pro Asn Ser Ser Leu
            85                  90                  95

Phe Trp Phe His Gln Leu Arg Phe Leu Asn Leu Ser His Asn Asn Phe
            100                 105                 110

Thr Ser Thr Ser Phe Pro Ser Glu Phe Gly Asn Leu Asn Lys Val Glu
        115                 120                 125

Val Leu Asp Leu Ser Phe Asn Ser Phe Thr Gly Gln Val Pro Ser Ser

```
            130                 135                 140
Phe Ser Asn Leu Ser Gln Leu Thr Glu Leu His Leu Ser Asn Asn Gln
145                 150                 155                 160

Leu Thr Gly Gly Phe Pro Gln Val Gln Asn Leu Thr Asn Leu Ser His
                165                 170                 175

Leu Asp Phe Glu Asn Asn Lys Phe Ser Gly Thr Val Pro Ser Ser Leu
            180                 185                 190

Leu Met Met Pro Phe Leu Ser Tyr Leu Asn Leu Tyr Gly Asn His Phe
        195                 200                 205

Thr Gly Ser Ile Glu Val Ser Thr Ser Ser Lys Leu Glu Ile Leu Tyr
    210                 215                 220

Leu Gly Leu Lys Pro Phe Glu Gly Gln Ile Leu Glu Pro Ile Ser Lys
225                 230                 235                 240

Leu Ile Asn Leu Lys Arg Leu Glu Leu Ser Phe Leu Asn Ile Ser Tyr
                245                 250                 255

Pro Leu Asp Leu Asn Leu Phe Ser Ser Leu Lys Ser Leu Thr Tyr Leu
            260                 265                 270

Asp Leu Ser Gly Asn Ser Ile Ser Pro Arg Ser Leu Arg Ser Asp Leu
        275                 280                 285

Tyr Ile Pro Leu Thr Leu Glu Lys Leu Leu Leu Glu Gln Cys Gly Ile
    290                 295                 300

Ile Glu Phe Pro Asn Ile Leu Lys Thr Leu Gln Lys Leu Glu Tyr Ile
305                 310                 315                 320

Asp Met Ser Asn Asn Arg Ile Asn Gly Lys Ile Pro Glu Trp Leu Trp
                325                 330                 335

Arg Leu Pro Arg Leu Arg Ser Met Ser Leu Ala Asn Asn Ser Phe Asn
            340                 345                 350

Gly Phe Glu Gly Ser Thr Asp Val Leu Val Asn Ser Ser Met Glu Ile
        355                 360                 365

Leu Phe Met His Ser Asn Asn Ile Gln Gly Ala Leu Pro Asn Leu Pro
    370                 375                 380

Leu Ser Ile Lys Ala Phe Ser Ala Gly Tyr Asn Asn Phe Ser Gly Glu
385                 390                 395                 400

Ile Pro Leu Ser Ile Cys Asn Arg Ser Ser Leu Ala Ala Leu Ser Leu
                405                 410                 415

Pro Tyr Asn Asn Phe Thr Gly Lys Ile Pro Gln Cys Leu Ser Asn Leu
            420                 425                 430

Thr Phe Val His Leu Arg Lys Asn Asn Leu Glu Gly Ser Ile Pro Asp
        435                 440                 445

Thr Leu Cys Ala Gly Asp Ser Leu Gln Thr Leu Asp Ile Gly Phe Asn
    450                 455                 460

Leu Ile Ser Gly Thr Leu Pro Arg Ser Leu Leu Asn Cys Ser Ser Leu
465                 470                 475                 480

Glu Phe Leu Ser Val Asp Asn Asn Arg Ile Lys Asp Thr Phe Pro Phe
                485                 490                 495

Trp Leu Lys Ala Leu Pro Asn Leu Gln Val Leu Ile Leu Ser Ser Asn
            500                 505                 510

Lys Leu Tyr Gly Pro Ile Ala Pro His Gln Ser Pro Leu Ala Phe
        515                 520                 525

Pro Glu Leu Arg Ile Phe Glu Ile Ala Asp Asn Met Phe Thr Gly Thr
    530                 535                 540

Leu Ser Pro Arg Tyr Phe Val Asn Trp Lys Thr Ser Ser Leu Thr Val
545                 550                 555                 560
```

```
Asn Glu Asp Gly Asp Leu Tyr Met Val Tyr Lys Asn Asn Ala Phe Gly
                565                 570                 575

Ile Asp Ser Tyr Val Tyr Arg Asp Thr Ile Asp Met Lys Tyr Lys Gly
            580                 585                 590

Leu Ser Met Glu Gln Gln Met Val Leu Asn Ser Tyr Ser Ala Ile Asp
        595                 600                 605

Phe Ser Gly Asn Arg Leu Glu Gly Gln Ile Pro Lys Ser Ile Gly Leu
    610                 615                 620

Leu Lys Glu Leu Ile Ala Leu Asn Leu Ser Asn Asn Ala Phe Thr Cys
625                 630                 635                 640

His Ile Pro Leu Ser Leu Ala Asn Ala Thr Glu Leu Glu Ser Leu Asp
            645                 650                 655

Leu Ser Arg Asn Gln Leu Ser Gly Thr Ile Pro Asn Gly Leu Lys Thr
            660                 665                 670

Leu Ser Phe Leu Ala Tyr Ile Asn Val Ser His Asn Lys Leu Lys Gly
        675                 680                 685

Glu Asn His Lys Glu His Arg Leu Leu Gly Asn Ile Asn Pro Pro Leu
        690                 695                 700

Lys Gly Met Gln Gly Phe Val Val Phe Leu Trp Arg Lys Leu Ala Leu
705                 710                 715                 720

Glu Arg Met Arg Arg Gln His Asn Asn Leu Arg Lys Lys Thr Lys Asn
            725                 730                 735

Arg Ser Lys Cys
            740
```